United States Patent [19]

Leong

[11] Patent Number: 5,165,925
[45] Date of Patent: Nov. 24, 1992

[54] VACCINE FOR IMMUNIZING FISH AGAINST INFECTIOUS PANCREATIC NECROSIS VIRUS

[75] Inventor: Jo-ann C. Leong, Albany, Oreg.

[73] Assignee: State of Oregon Acting by and Through the State Board of Higher Education on behalf of Oregon State University, Eugene, Oreg.

[21] Appl. No.: 346,623

[22] Filed: May 2, 1989

[51] Int. Cl.$^5$ ............................................. A61K 39/00
[52] U.S. Cl. ....................................... 424/88; 424/89; 435/69.3
[58] Field of Search ..................... 424/88, 89; 530/350, 530/857; 435/69.3

[56] References Cited

PUBLICATIONS

Caswell-Ruo et al "Monoclonal Antibodies to Infectious Pancreatic Necrosis Virus . . . " J. Gen. Virology v. 67, pp. 2193-2205 (1986).

Mertens & Dobos "Messenger RNA of Infectious Pancreatic Necrosis Virus is Polycioxmic" Nature vol. 297, pp. 243-246, May, 1982.

Duncan et al "Synthesis of the Infectious Pancreatic Necrosis Virus Polyprotein . . . " J. of Virology vol. 61(12) pp. 3655-3664, Dec. 1987.

Dorson, "Infectious Pancreatic Necrosis Virus of Salmonids: Overview of Current Problems," in *Antigens of Fish Pathogens* (ed. by D. P. Anderson, M. Dorson and P. H. Dubourget) Collection Foundation Marcel Merieux, Lyon, pp. 7-32 (1982).

Okamato et al., *Journal of Fish Diseases*, 6:19-25 (1983).

Dorson et al., "Infectious Pancreatic Necrosis Virus of Salmonids: Biological and Antigenic Features of a Pathogen Strain and of a Non-pathogenic Variant Selected in RTG-2 Cells," *Journal of Fish Diseases*, 1:309-320 (1978).

Darragh and MacDonald, "A Host Range Restriction in Infectious Pancreatic Necrosis Virus Maps to the Large RNA Segment and Involves Virus Attachment to the Cell Surface," *Virol.* 123:264-272 (1982).

Hedrick et al., "Biochemical Characterization of Eel Virus European," *J. Gen. Virol.* 64:1421-1426 (1983).

Okamoto et al., "Antigenic Relationships of Selected Strains of Infectious Pancreatic Necrosis Virus and European Eel Virus," *J. Fish. Dis.* 6:19-25 (1983).

Espinoza et al., "Identity Between Infectious Pancreatic Necrosis Virus VR-299 and a Chilean Isolate," *Intervirology* 24:58-60 (1985).

Somogyi and Dobos, "Virus-Specific RNA Synthesis in Cells Infected by Infectious Pancreatic Necrosis Virus," *J. Virol.* 33:129-139 (1980).

(List continued on next page.)

Primary Examiner—David L. Lacey
Assistant Examiner—Nina Ossanna
Attorney, Agent, or Firm—Klarquist, Sparkman, Campbell, Leigh & Whinston

[57] ABSTRACT

A vaccine for simultaneously immunizing large numbers of fish against infection by Infection Pancreatic Necrosis Virus (IPNV) is disclosed. The vaccine comprises viral capsid polypeptides produced from a recombinant expression vector in a compatible bacterial host. The expression vector includes IPNV cDNA sequences encoding at least a portion of a capsid protein of IPNV, the portion capable of inducing immunity in susceptible fish to subsequent IPNV infection. A vaccine containing both capsid proteins of IPNV is particularly effective. The vaccine is administered by preparing a crude lysate from bacterial cells having the vector and adding the lysate to the water containing young fish. For the first time, large numbers of fish can be immunized against IPNV infection without having to inject vaccine into each fish.

9 Claims, 17 Drawing Sheets

OTHER PUBLICATIONS

McAllister and Owens, "Infectious Pancreatic Necrosis Virus: Protocol for a Standard Challenge to Brook Trout," *Trans. Amer. Fisheries Soc.* 115:466–470 (1986).

MacDonald and Dobos, "Identification of the Proteins Encoded by Each Genome Segment of Infectious Pancreatic Necrosis Virus," *Virol.* 114:414–422 (1981).

Mertens et al., "In Vitro RNA Synthesis by Infectious Pancreatic Necrosis Virus-Associated RNA Polymerase," *J. Gen. Virol.* 59:47–56 (1982).

Duncan and Dobos, "The Nucleotide Sequence of Infectious Pancreatic Necrosis Virus (IPNV) dsRNA Segment A Reveals One Large ORF Encoding a Precursor Polyprotein," *Nucl. Acids Res.* 14:5934 (1986).

Nagy et al., "Mapping of the Large RNA Genome Segment of Infectious Pancreatic Necrosis Virus by Hybrid Arrested Translation," *Virol.* 158:211–217 (1987).

Huang et al., "A Physical Map of the Viral Genome for Infectious Pancreatic Necrosis Virus Sp: Analysis of Cell-Free Translation Products Derived from Viral cDNA Clones," *J. Virol.* 60:1002–1011 (1986).

"The Fish Doctors," *Oregon Business*, p. 127 (Feb. 1988).

Cone, J., "Viral Vaccines for Fish Promising", *Oregonian* (Thursday, Mar. 23, 1989).

Manning, D. S., "Deletion Mapping and Expression of the Large Genomic Segment of Infectious Pancreatic Necrosis Virus," PhD Thesis, Oregon State University (1988).

Barrie, R. J., "Characterization of an Immunoreactive Region of the Major Capsid Protein for IPNV," Masters Thesis, Oregon State University (1988).

PARTIAL RESTRICTION MAP OF Sp cDNA CLONES
SEGMENT A

A=Ava I  Ac=Acc I  E=EcoRI  K=Kpn I  N=Nco I
Nd=Nde I  X=Xho I

▶ Lac_p ..... ATG/ACC/ATG/ATT/ACG/CCA/AGC/TTG/GAT/GCC/TGC/AGG
                                                         Pstl

GGG/GGG/GGT/CTA/TAT/CAA/TGC/AAG/ATG....A SEGMENT ORF....

Table of Amino Acids

```
A = Alanine
C = Cysteine
D = Aspartic Acid
E = Glutamic Acid
F = Phenylalanine
G = Glycine
H = Histidine
I = Isoleucine
K = Lysine
L = Leucine
M = Methionine
N = Asparagine
P = Proline
Q = Glutamine
R = Arginine
S = Serine
T = Threonine
V = Valine
W = Tryptophan
Y = Tyrosine
```

SEQUENCE OF THE VP2 GENE OF THE SP STRAIN OF IPNV

```
1    TTG GGC TGC AGG GGG GGG GGT CTA TAT CAA TGC AAG ATG AAC    42
                                                     M   N

43   ACA AAC AAG GCA ACC GCA ACT TAC TTG AAA TCC ATT ATG CTT    84
      T   N   K   A   T   A   T   Y   L   K   S   I   M   L

85   CCA GAG ACT GGA CCA GCA AGC ATC CCG GAC GAC ATA ACG GAG    126
      P   E   T   G   P   A   S   I   P   D   D   I   T   E

127  AGA CAC ATC TTA AAA CCA GAG ACC TCG TCA TAC AAC TTA GAG    168
      R   H   I   L   K   P   E   T   S   S   Y   N   L   E

169  GTC CCC GAA TCA GGA AGT GGC ATT CTT GTT TGT TTC CCT GGG    210
      V   P   E   S   G   S   I   L   V   C   F   P   G

211  GCA CCA GGC TCA CGG ATC GGC GCA CAC TAC AGA TGG AAT GCG    252
      A   P   G   S   R   I   G   A   H   Y   R   W   N   A

253  AAC CAG ACG GGG CTG GAG TTC GAC CAG TGC TGG AGA GCG TCG    294
      N   Q   T   G   L   E   F   D   Q   C   W   R   A   S

295  CAG GAC CTG AAG AAA GCC TTC AAC TAC GGG AGG CTG ATC TCA    336
      Q   D   L   K   K   A   F   N   Y   G   R   L   I   S

337  AGG AAA TAC GAC ATT CAA AGC TCC ACA CTA CCG GCC GGT CTC    378
      R   K   Y   D   I   Q   S   S   T   L   P   A   G   L

379  TAT GCT CTG AAC GGG ACG CTC AAC GCT GCC ACC TTT GAA GGC    420
      Y   A   L   N   G   T   L   N   A   A   T   F   E   G

421  AGT CTG TCT GAG GTG GAG AGC CTG ACC TAC AAT AGC CTG ATG    462
      S   L   S   E   V   E   S   L   T   Y   N   S   L   M

463  TCC CTA ACT ACG AAC CCC CAG GAC AAA GCC AAC AAC CAG CTG    504
      S   L   T   T   N   P   Q   D   K   A   N   N   Q   L
```

FIG. 15A

```
505  GTG ACC AAA GGA GTC ACC GTC CTG AAT CTA CCA ACA GGG TTC  546
      V   T   K   G   V   T   V   L   N   L   P   T   G   F

547  GAC AAA CCA TAC GTC CGC CTA GAG GAC GAG ACA CCC CAG GGT  588
      D   K   P   Y   V   R   L   E   D   E   T   P   Q   G

589  CTC CAG TCA ATG AAC GGG GCC AGG ATG AGG TGC ACA GCT GCA  630
      L   Q   S   M   N   G   A   R   M   R   C   T   A   A

631  ATT GCA CCA CGG AGG TAC GAG ATC GAC CTC CCA TCC CAA AGC  672
      I   A   P   R   R   Y   E   I   D   L   P   S   Q   S

673  CTA CCC CCC GTT CCT GCG ACA GGA ACC CTG ACC ACT CTC TAC  714
      L   P   P   V   P   A   T   G   T   L   T   T   L   Y

715  GAG GGA AAC GCC GAC ATC GTC AAC TCC ACA ACA GTG ACG GGA  756
      E   G   N   A   D   I   V   N   S   T   T   V   T   G

757  GAC ATA AAC TTC AGT CTG GCA GAA CAA CCC GCA AAC GAG ACC  798
      D   I   N   F   S   L   A   E   Q   P   A   N   E   T

799  AGG TTC GAC TTC CAG CTG GAC TTG ATG GGC CTT GAC AAT GAC  840
      R   F   D   F   Q   L   D   L   M   G   L   D   N   D

841  GTC CCA GTG GTC ACA GTG GTC AGC TCC GTG CTG GCC ACA AAC  882
      V   P   V   V   T   V   V   S   S   V   L   A   T   N

883  GAC AAC TAC AGA GGA GTC TCA GCC AAG ATG ACC CAG TCC ATC  924
      D   N   Y   R   G   V   S   A   K   M   T   Q   S   I

925  CCG ACC GAG AAC ATT ACC AAG CCG ATC ACC AGG GTC AAG CTG  966
      P   T   E   N   I   T   K   P   I   T   R   V   K   L

967  TCA TAC AAG ATC AAC CAG CAG ACA GCA ATC GGC AAT GTC GCC  1008
      S   Y   K   I   N   Q   Q   T   A   I   G   N   V   A

1009 ACC CTG GGC ACA ATG GGT CCA GCA TCC GTC TCC TTT TCA TCG  1050
      T   L   G   T   M   G   P   A   S   V   S   F   S   S

1051 GGG AAC GGA AAT GTC CCC GGC GTG CTC AGA CCA ATC ACA CTG  1092
      G   N   G   N   V   P   G   V   L   R   P   I   T   L

1093 GTG GCA TAT GAG AAG ATG ACA CCG CTG TCC ATC CTG ACC GTA  1134
      V   A   Y   E   K   M   T   P   L   S   I   L   T   V

1135 GCT GGA GTG TCC AAC TAC GAG CTG ATC CCA AAC CCA GAA CTC  1176
      A   G   V   S   N   Y   E   L   I   P   N   P   E   L

1177 CTC AAG AAC ATG GTG ACA CGC TAT GGC AAG TAC GAC CCC GAA  1218
      L   K   N   M   V   T   R   Y   G   K   Y   D   P   E
```

FIG. 15B

```
1219  GGT CTC AAC TAT GCC AAG ATG ATC CTG TCC CAC AGG GAA GAG  1260
       G   L   N   Y   A   K   M   I   L   S   H   R   E   E

1261  CTG GAC ATC AGG ACA GTG TGG AGG ACA GAG GAG TAC AAG GAG  1302
       L   D   I   R   T   V   W   R   T   E   E   Y   K   E

1303  AGG ACC AGA GTC TTC AAC GAA ATC ACA GAG AAG ACC AGT GAC  1344
       R   T   R   V   F   N   E   I   T   E   K   T   S   D

1345  CTG CCC ACG TCA AAG GCA TGG GGC TGG AGA GAC ATA GTC AGA  1386
       L   P   T   S   K   A   W   G   W   R   D   I   V   R

1387  GGA ATT CGA AAA ATC GCA GCT CCT GTA CTG TCC ACG CTG TTT  1428
       G   I   R   K   I   A   A   P   V   L   S   T   L   F

1429  CCA ATG GCA GCA CCA CTC ATA GGA ACG GCA GAC CAA TTC ATT  1470
       P   M   A   A   P   L   I   G   T   A   D   Q   F   I

1471  GGA GAT CTC ACC AAG ACC AAC GCA GCA GGC GGA AGG TAC CAC  1512
       G   D   L   T   K   T   N   A   A   G   G   R   Y   H  ← Probable end
                                                                  of VP2 gene
1513  TCC ATG GCC GCA GGA GGG CGC TAC AAA GAC GTG CTC GAG TCC  1554
       S   M   A   A   G   G   R   Y   K   D   V   L   E   S
```

FIG. 15C

VACCINE FOR IMMUNIZING FISH AGAINST INFECTIOUS PANCREATIC NECROSIS VIRUS

This invention was made with government support under the following grant numbers awarded by the U.S. Department of Commerce, National Oceanic and Atmospheric Administration, Science and Education Administration: NA81AA-D-00086 (1982-85, Recombinant DNA Technology in Aquaculture, Project No. R/FSD-9, Oregon State University); NA85AA-D-SG-095 (1985-87, Development of a Subunit Vaccine for IPNV, Project No. R/FSD-11, Oregon State University); and NA85AA-D-SG-095 (1987-89, Control of Virus Diseases in Fish, Project No. R/FSD-13, Oregon State University). The government has certain rights in this invention.

BACKGROUND OF THE INVENTION

1. Field of the Invention

This invention relates to the control of viral infections of fish and more specifically to vaccines for controlling outbreaks of infectious pancreatic necrosis virus infections in fish populations. 2. General Discussion of the Background It is estimated that fish diseases cost twenty to thirty cents for each dollar spent rearing fish in the United States. Although fish pathogens include fungal, protozoan and bacterial agents, it is the viral diseases that most concern hatchery managers and fisheries scientists because they are largely uncontrollable. There are no antibiotic agents that work effectively against viruses in fish.

Infectious pancreatic necrosis (IPN), a contagious viral disease in fish, causes morbidity and mortality in juvenile rainbow trout, Atlantic salmon and brook trout. The virus, infectious pancreatic necrosis virus (IPNV), has been isolated from both salmonid and non-salmonid species of fish lacking pathogenic symptoms. In survivors of an IPNV epizootic, the virus persists and can cause severe growth retardation in individual fish exhibiting virus persistence. McKnight and Roberts, *Br. Vet. J.* 132: 76-86, 1976. In smolts, the virus produces considerable necrosis or inflammation of the pancreas. The virus is capable of infecting a number of different hosts and has a worldwide presence. Pilcher and Fryer, *Crit. Rev. Microbiol.* 7:287-364, 1980.

IPN disease in a brook trout hatchery was first reported in 1941. McGonigle, *Trans. Am. Fish. Soc.* 70:297, 1941. In 1960, the viral nature of the disease was confirmed. Wolf et al., *Proc. Soc. Exp. Biol. Med.* 104:105-110, 1960. Since that time there have been isolations of the virus in a variety of fish species throughout the world, including various trout and salmon species, carp, perch, pike, eels and char, as well as mollusks and crustaceans. Acute disease has been reported primarily in a limited number of salmonid species, such as trout and salmon. Many of these species are of growing economic importance and since mortalities range as high as 90 percent, Pilcher and Fryer, *Crit. Rev. Microbiol.* 7:287-364, 1980, an IPN outbreak in a hatchery can be an economic disaster for the aquaculturist.

Young fish (two- to four-month old) appear to be the most susceptible to IPNV infection, resulting in high mortality. Wolf et al., U.S. Dept. Int. Bur. Sport Fish. and Wildlife, Fish Disease Leaflet 1:14, 1966; Frantsi and Savan, *J. Wildlife Dis.* 7:249-255, 1971. In trout, IPN usually attacks young fry about five to six weeks after their first feeding. The affected fish are darker than usual, have slightly bulging eyes and often have swollen bellies. At the beginning of an outbreak, large numbers of slow, dark fry are seen up against water outflows, and fish are seen "shivering" near the surface. The shivering results from a characteristic symptom of the disease, a violent whirling form of swimming in which the fish rotate about their long axis. If the affected fish are opened up, a characteristic white mucus is seen in the stomach. The pancreas appears to be the primary target organ for the virus, with the pancreatic fat cells or Islets of Langerhans being unaffected. McKnight and Roberts, *Br. Vet. J.* 132:76-86, 1976. The intestine is the only organ besides the pancreas where viral lesions are consistently found.

After an IPN outbreak, the surviving fish generally become carriers of the virus. For example, trout that are carriers of the virus are a serious problem for the aquaculture industry because the only control method currently available for eliminating the virus in carrier fish is complete destruction of these fish. Several factors, including age, species and water temperature, appear to influence the severity of infection and the subsequent establishment of the carrier state. Surviving carriers shed infectious IPNV which is detectable in fecal and sex products of the fish for the remainder of their lifetime. Billi and Wolf, *J. Fish. Res. Bd. Can.* 26:1459-1465, 1969; Yamamoto, *Can. J. Micro.* 21:1343-1347, 1975; Reno et al., *J. Fish. Res. Bd. Can.* 33:1451-1456, 1978.

The persistence of the virus in carrier fish appears to be the result of continued virus production by a small number of infected cells in certain organs. Only a few cells in the infected organs are capable of registering as infectious centers that actually produce virus. Hedrick, Ph.D. Thesis, "Persistent Infections of Salmonid Cell Lines With Infectious Pancreatic Necrosis Virus: A Model for the Carrier State in Trout," Oregon State University, 1980.

IPNV is a birnavirus whose genome consists of two segments of double-stranded RNA. Dobos, *Nucl. Acids Res.* 3:1903-1919, 1976; Dobos, *J. Virol.* 21:242-258, 1977. The viral genome is contained within a non-enveloped icosahedral capsid approximately 60 nm in diameter. The larger "A" segment has a molecular weight of $2.5 \times 10^6$ Daltons (Da) and encodes at least three proteins whose order in the genome from the N (5') terminus is $\beta$(VP2) (approximately 54 kDa, major capsid protein) - $\gamma_2$ (NS) (approximately 27.5 kDa, non-structural protein having proteolytic activity) - $\gamma_1$ (VP3) (approximately 31 kDa, minor capsid protein), as shown in FIG. 1. Chang et al., *Can. J. Microbiol.* 24:19-27, 1978; Huang et al., *J. Virol.* 60:1002-1011, 1986. These proteins are encoded on a single mRNA within the infected cell. Mertens and Dobos, *Nature* 297:243-246, 1982. Sequence analysis has indicated that there is one continuous open reading frame for this viral RNA segment. Duncan and Dobos, *Nucleic Acids Res.* 14:5934-5935, 1986.

Currently, there are no methods for controlling IPN except the destruction of infected stocks and the decontamination of hatchery facilities. Despite a great deal of interest in developing a vaccine for IPNV and investigation of a variety of approaches, little progress has been made toward a truly practical vaccine. One approach has been the use of attenuated viral strains. See, Dorson, Abstract, International Conference on IPNV, Taloires, France, 1982. Unfortunately, the attenuated strains either fail to infect the fish or fail to induce protection. Strains with low virulence have been tested as vaccines for more virulent strains, but mortality from the vaccinating strain was either too high or protection was only moderate. Hill et al., "Studies of the Immunization of Trout Against IPN," in *Fish Diseases*, Third COPRAQ Session (W. Ahne, ed.), NY, pp. 29-36, 1980. Major unsolved requirements associated with the use of live, attenuated virus vaccines include: the requirement for stability of attenuation and the development of appropriate tests to assess this stability; the requirement that the virus should not establish persistent infection in the host; and the requirement that the virus should exhibit low communicability in field trials.

Use of killed virus as vaccines has also been tried. For example, if formalin-inactivated virus is injected intraperitoneally into four week post-hatch fry, the fish become immunized. Dorson, *J. Virol.* 21:242-258, 1977. However, neither immersion of the fish into a liquid suspension of killed virus nor oral administration thereof was effective. The main problem with using killed virus is the lack of a practical method for administration of the vaccine. Injection is impractical for large numbers of immature fish. Some investigators have suggested that the uptake of viral antigen by immersion might be improved if the virus was disrupted into smaller, sub-viral components, but viral disruption methods have resulted in loss of antigenicity. Hill et al., 1980 (supra); Hill and Way, "Serological Classification of Fish and Shellfish Birnaviruses," Abstract, First International Conference of the European Association of Pathology, Plymouth, England, 1983.

The preparation of a killed virus vaccine is very expensive. In addition, both attenuated and killed virus vaccines must be extensively purified in order to prevent cellular contamination. All of these requirements add to the cost of developing and preparing a viral vaccine by conventional methods. For fish hatcheries that operate o relatively thin profit margins, the additional expense of such vaccines is prohibitive.

Accordingly, there remains no known practical method of immunizing fish against IPNV infection, despite the need for such a method. Hence, there is a need for a method for: (1) producing sufficient quantities of a non-infectious IPNV immunogen that can be simultaneously administered to large numbers of fish; (2) a method for producing such viral immunogen in large quantities at a reasonable cost; (3) producing such viral antigen that is completely free of viable virus; and (4) administering such viral antigen to fish as early in their development cycle as possible.

SUMMARY OF THE INVENTION

It has now been discovered that fish can be immunized simultaneously in large numbers against IPNV infections by the administration of a vaccine comprising the IPNV VP2 polypeptide (major capsid protein) or an immunogenic portion of VP2. Further, a vaccine comprising both the major and minor capsid proteins is particularly effective. Such vaccines can be mass-produced by the culturing of bacterial host cells that contain expression vectors including IPNV cDNA sequences coding for the viral polypeptides in the vaccine. The expression vectors produce the corresponding viral protein or an immunogenic portion thereof in the bacteria when the bacterial cells are cultured under appropriate conditions. After a defined culture period, the bacterial cells are disrupted to release the viral proteins produced in the cells. For use as a fish vaccine, the cell lysate containing the viral proteins may be used without further purification of the viral proteins. In other words, the bacterial lysate containing viral proteins is added directly to the water containing the fish.

By such molecular cloning methods, it is now possible to provide an inexpensive, subunit vaccine for immunizing fish against IPNV infection, such vaccine having none of the drawbacks of live viral vaccines, attenuated viral vaccines, or killed virus vaccines, the problems of recombination and reversion to virulence being eliminated. Additionally, the vaccine of the present invention may be administered simultaneously to large numbers of fish, conferring immunity to those fish without having to individually inject the vaccine into each fish. Moreover, with efficient expression of the viral protein in bacterial cells, vaccine production becomes very inexpensive in contrast to production costs associated with a killed or attentuated viral vaccine.

Specifically, subunit vaccines to IPNV infection in fish have now been developed by recombinant DNA techniques. Complementary DNA to the viral "A" segment RNA has been constructed and cloned in appropriate expression vectors. Further, complementary DNA sequences representing terminal deletions of the viral "A" segment have also been constructed and cloned in appropriate expression vectors. Susceptible bacterial cells transformed with these recombinant expression vectors have been found to produce viral capsid polypeptides that are capable of inducing immunity in susceptible fish when added to water containing the fish. Further, certain non-posttranslationally modified polypeptides produced from expression vectors containing deletions are also capable of inducing immunity in fish. This invention represents a major step forward in IPNV vaccine technology because viral proteins obtained from disrupted virions are incapable of inducing immunity in fish unless they are injected into the body of each fish. The present invention allows large quantities of IPNV capsid proteins to be synthesized in bacteria and used to immunize fish against IPNV infection. The result is a safe, inexpensive vaccine for fish against IPN virus.

Accordingly, an object of the present invention is to provide a method for inexpensively producing large quantities of immunogenic IPNV proteins.

Another object is to provide a method for producing immunogenic IPNV protein not containing any viable virus.

Another object is to provide a method of producing immunogenic IPNV protein that does not cause viral infection upon immunizing fish therewith.

Another object is to provide a method for immunizing large numbers of fish as early in their developmental cycle as possible against IPNV infection.

Another object is to provide a method for producing an IPNV subunit vaccine, the antigenicity of which has been deliberately manipulated for optimal effect.

Another object is to provide a vaccine against IPNV infection that cannot revert to a virulent state.

Another object is to provide such a vaccine that is effective in interrupting the vertical transmission of IPNV infection by immunizing brood stock fish.

BRIEF DESCRIPTION OF THE DRAWINGS

FIG. 15 is the nucleotide sequence of the VP2 gene of the SP strain of IPNV as well as the amino acid sequence of the corresponding VP2 protein as deduced from the nucleotide sequence.

DETAILED DESCRIPTION

Figure 1:
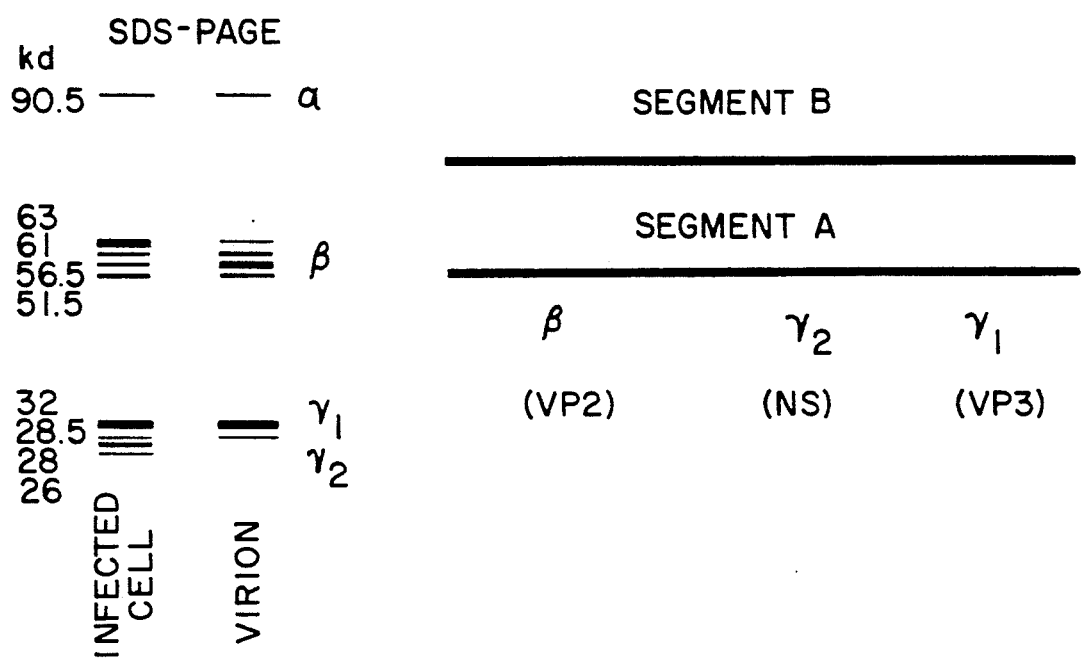
FIG. 1 is a schematic representation of the IPNV RNA genome and proteins. The lanes on the left show the relative migrations of virion protein and viral proteins from infected cell lysates in SDS-polyacrylamide gels.

Subunit vaccines for immunizing fish against IPNV are produced by first cleaving DNA complementary to the "A" segment of the viral RNA genome using a nuclease to remove sequences 5' to the initiation codon of the large open reading frame. The nuclease-digested cDNA is then combined with an appropriate expression vector and screened for open reading frame fusions. Cells of an appropriate bacterial host are transformed with the expression vector, resulting in the replication and expression of viral genes in bacterial host cells. Bacterial transformants are screened immunologically for the expression of viral proteins. Colonies expressing viral capsid proteins are cultivated to high number and subsequently lysed to produce cellular extracts containing viral proteins. The extract can then be added to water containing young fish who become immune thereby to subsequent infection by the virus.

A. Virus Growth and Purification

The appropriate strain of IPN virus is propagated in CHSE-214 cells (Fryer et al., Ann. N.Y. Acad. Sci. 126:566–586, 1965) at a multiplicity of infection of 0.05–0.1 pfu/cell. Cell monolayers are grown at 16°–18° C. in glass bottles using Eagle's minimal essential media (MEM) with Earle's salts (Gibco) supplemented with 0.11-percent bicarbonate, 10-percent fetal bovine serum, 100 IU/mL penicillin, 100 micrograms/mL (μg/mL) streptomycin (Gibco), and 10 μg/mL gentamicin sulfate (Sigma). Virus particles are harvested 3–5 days post-infection. After an initial low-speed centrifugation to remove cellular debris (5000 rpm, 4° C., for 5 minutes in a Sorvall GSA rotor), the virus are pelleted in a Beckman Type 35 rotor at 30,000 (30K) RPM for 90 minutes and resuspended in SM buffer (0.1 M NaCl; 8 mM $MgSO_4$; 20mM Tris-HCl, pH 7.5; 0.01-percent gelatin) or TBS (20 mM Tris-HCl, 500 mM NaCl, pH 7.5). The virus is initially purified by centrifugation through a step gradient consisting of 5 mL of 1.4 g/cm$^3$ CsCl, 3 mL of 1.25 g/cm$^3$ CsCl, and 1.7 mL of 20-percent sucrose in SM buffer or TBS in either a Beckman SW41 or SW50.1 rotor at 35K for 90 minutes. Intact virions band at a density of 1.33 g/cm$^3$, empty capsids at 1.29 g/cm$^3$. The viral band is collectable by side puncture. Intact virions are further purified by isopycnic density gradient centrifugation in 1.33 g/cm$^3$ CsCl for 14–16 hours at 35K RPM at 4° C. Intact virus is collected by side puncture or from above using a Buchler Densi-flo IIC fraction collector. The volume of CsCl containing the virus is diluted with SM buffer and the virus pelleted at 35K for 90 minutes in a SW41 rotor at 4° C.

B. Preparation of Viral RNA

The viral pellet is resuspended in TE buffer (10 mM Tris-HCl, pH 8.0; 1 mM EDTA) containing 0.5-percent sodium dodecyl sulfate (SDS) and 100 μg/mL proteinase K and left at room temperature overnight or at 65° C. for 2 hours. The RNA is extracted twice with an equal volume of phenol/0.1-percent 8-hydroxyquinoline and then twice with chloroform/isoamyl alcohol, followed by precipitation in ethanol.

C. Poly-A Tailing of Viral RNA

Polyadenylate tails ranging in length between 40–80 bases are added to the 3'-ends of the viral double-stranded RNA (dsRNA) using E. coli poly-A polymerase. Sipple, Eur. J. Biochem. 37:31–40, 1973. The reaction is performed in 25 microliters (μL) at 37° C. (250 mM NaCl; 50 mM Tris-HCl, pH 8.0; 10 mM $MgCl_2$; 2.5 mM $MnCl_2$; 50 μg/mL bovine serum albumin; 0.1 mM [$^3$H]-ATP; 15 μg dsRNA; 3.5 units poly-A polymerase). After 40 minutes, the reaction mixture is extracted with phenol and with chloroform/isoamyl alcohol followed by precipitation in ethanol in the presence of 2 M ammonium acetate.

D. First Strand cDNA Synthesis

Eight to 10 µg of poly-A tailed viral RNA is resuspended in 20 µL sterile distilled water (treated with 0.3-percent diethylpyrocarbonate), boiled for three minutes, and then chilled on ice. The reaction volume is raised to 200 µL containing 50 µg/mL oligo(dT)$_{12}$; 80 µg/mL actinomycin D; 2 mM each of dATP, dGTP and TTP; 100 µM [α-$^{32}$P]-dCTP (specific activity=4 Ci/mmole); 50 mM Tris-HCl, pH 8.3; 10 mM MgCl$_2$; 10 mM dithiothreitol (DTT); and 13 units/µg RNA of avian myeloblastosis virus reverse transcriptase. After incubation at 42° C. for 3-4 hours, the reaction is stopped by the addition of EDTA and SDS. The RNA/cDNA hybrid is extracted with phenol and then chloroform/isoamyl alcohol as described above. The nucleic acid is precipitated in ethanol twice in the presence of 2 M ammonium acetate prior to second strand cDNA synthesis.

E. Second Strand cDNA Synthesis

The RNA/cDNA hybrid nucleic acid is converted into dsDNA by a modification of the method of Okayama and Berg (*Mol. and Cell Biol.* 2:161-170, 1982). This method employs *E. coli* DNA polymerase I and RNase H at concentrations of 30 units and 1 unit/µg cDNA, respectively, plus 50 units/mL *E. coli* DNA ligase. The nucleic acid is resuspended in a reaction volume of 100 µL containing the enzyme concentrations indicated above in a solution of 100 mM HEPES (N-2-hydroxyethylpiperazine-N'-2-ethanesulfonic acid), pH 6.9; 4 mM MgCl$_2$: 15 mM β-mercaptoethanol; 70 mM KCl; 2 mM each dCTP, dGTP, dATP; 50 µM [α-$^{32}$P]-TTP (final specific activity=1 Ci/mmole); and 15 82 M β-nicotinamide adenine dinucleotide. The reaction is incubated successively at 12° C. and at room temperature for one hour each and terminated with EDTA and sodium dodecyl sulfate (SDS). Ethanol precipitation in the presence of 2 M ammonium acetate is performed twice to eliminate free dNTP from the ds cDNA prior to poly-dC tailing.

F. Transformation of cDNA

Figure 2:
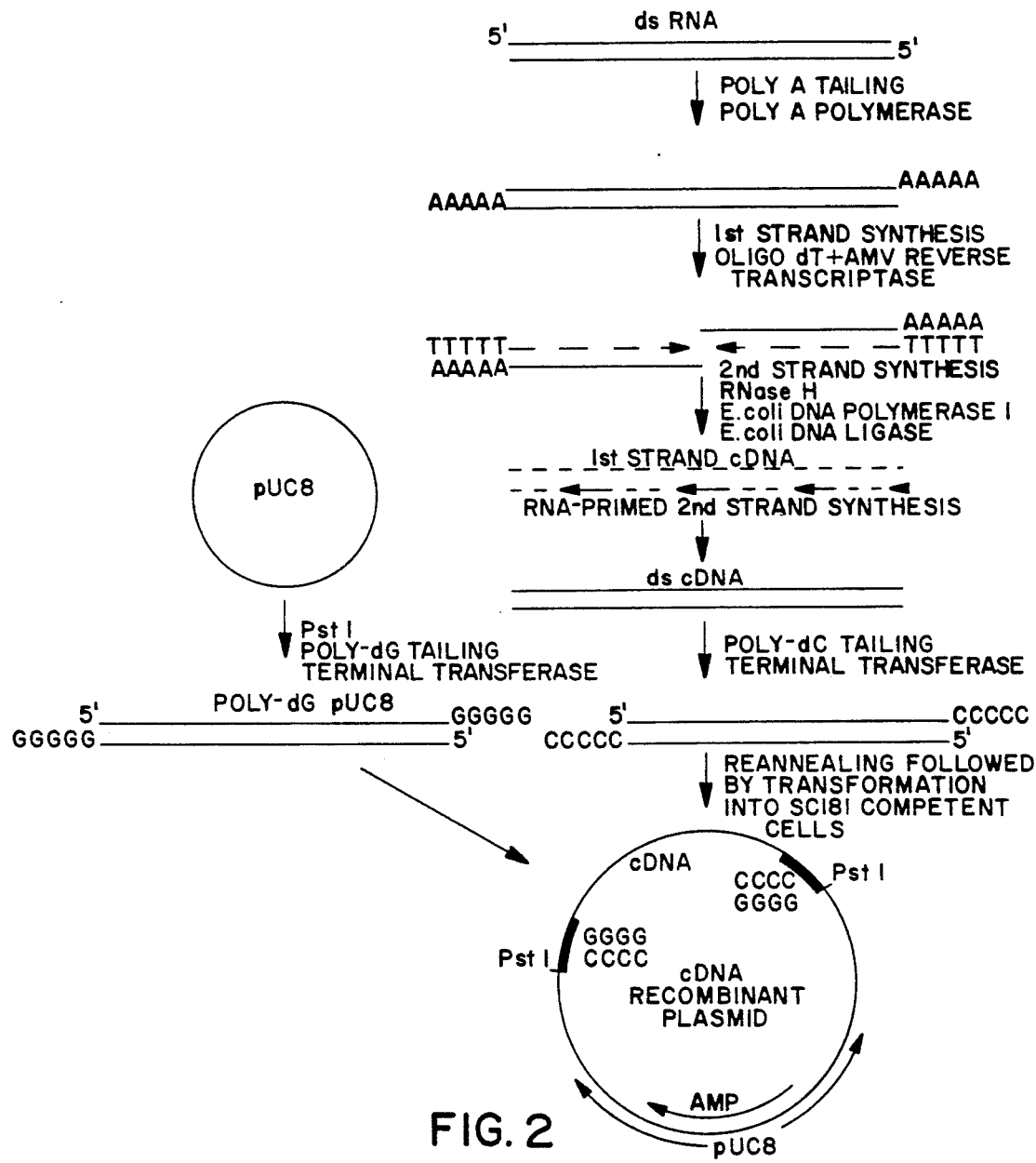
FIG. 2 schematically depicts a cloning strategy for producing IPNV cDNA recombinant plasmids.

Complementary homopolymer tails of approximately 15-20 bases are added to the cDNA (poly-dC) and to PstI-cut plasmid vector pUC8 (poly-dG) using terminal deoxynucleotide transferase. Insert and vector DNA's are reannealed at 42° C. for several hours and transformed into calcium chloride-treated *E. coli* host strain SC181 (Appleyard, *Genetics* 39:440-452, 1954) by the method of Maniatis et al., *Molecular Cloning: A Laboratory Manual*, Cold Spring Harbor Laboratory, 1982. Transformants are isolated by plating onto LB agar supplemented with 120 µg/mL ampicillin. The cloning strategy is depicted schematically in FIG. 2.

G. Preparation of cDNA Probes For Screening cDNA Transformants

Two µg of viral genomic RNA are radiolabeled with avian myeloblastosis virus (AMV) reverse transcriptase. The RNA with added calf-thymus primer DNA (Taylor et al., *Biochim. Biophys. Acta* 442:324-330, 1976) is denatured by boiling in sterile distilled water for 2 minutes and then quickly cooled in an ice water bath. The reaction volume is raised to 30 µL containing 50 mM Tris-HCl, pH 8.3; 60 mM KCl; 10 mM MgCl$_2$; 5 mM DTT; and 50 µCi [$^{32}$P]-dCTP (specific activity=3200 Ci/mmole) and incubated at 42° C. for 2 hours. EDTA is then added and the labeled cDNA purified by Sephadex G-50 column chromatography.

H. Screening cDNA Transformants Using Colony Blots

The cDNA transformants are examined for viral sequences using the screening method of Maniatis et al. (supra, 1982). Bacterial colonies are picked onto nitrocellulose filter papers overlaying LB agar with 120 µg/mL ampicillin. The filters are incubated at 37° C. overnight and the colonies lysed by sequential treatment of the filters with 10-percent SDS; 0.5 M NaOH and 1.5 M NaCl; 0.5 M Tris-HCl, pH 8.0 and 1.5 M NaCl; and 2×SSPE (0.36 M NaCl; 20 mM NaH$_2$PO$_4$, pH 7.4; 2 mM EDTA, pH 7.4). After baking for 2 hours at 80° C., the filters are treated with prehybridization buffer comprised of 6×SSPE, 50-percent formamide, 0.5-percent SDS, 1-percent glycine, 5×Denhardt's solution, and 200 µg/mL denatured salmon sperm DNA. Hybridization is performed at 42° C. for 12 hours with the same buffer without glycine and containing approximately 1×10$^6$ CPM/mL of the $^{32}$P-labeled probe.

I. Preparation of Plasmid DNA From cDNA Transformants

Two techniques can be employed for either the analysis of plasmid DNA by agarose gel electrophoresis or for the production of large quantities of DNA. Overnight colonies of cDNA transformants are treated with an alkaline/SDS buffer for direct gel electrophoresis (Kurath et al., *J. Virol.* 53:469-476, 1985). Alternatively, the boiling method of Holmes and Quigley (*Anal. Biochem.* 114:193-197, 1981) is used for large scale DNA purification.

J. Restriction Enzyme Analysis of cDNA Transformants

Restriction maps are determined for those cDNA transformants positively identified by colony blots hybridized with viral cDNA probes. After initial size screening for insert size with PstI, many different restriction enzymes may be used to determine the location of overlapping sequences. Enzyme reactions are performed as described by the manufacturers thereof using 500 nanograms (ng) of plasmid DNA per reaction.

Figure 3:
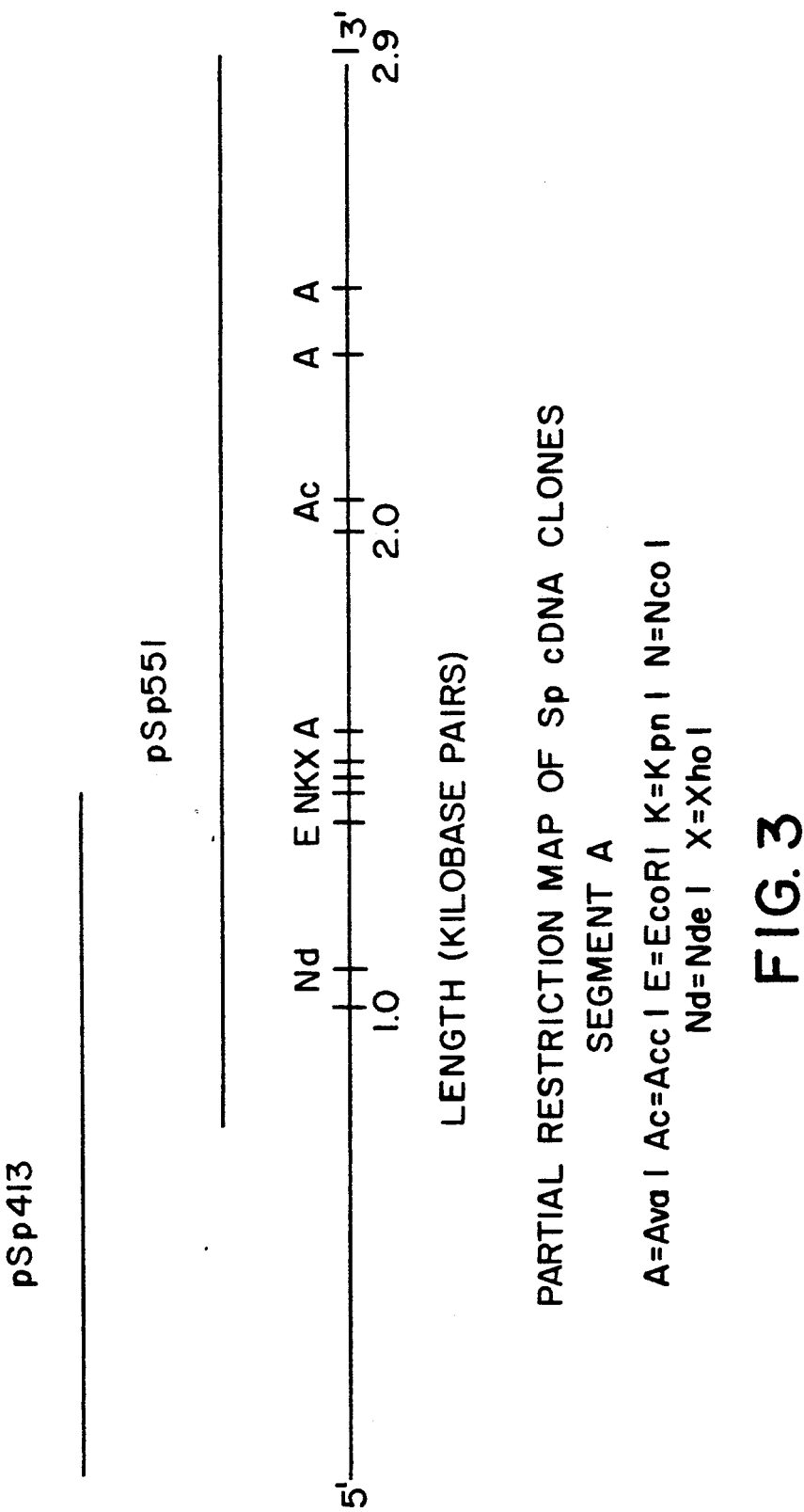
FIG. 3 is a schematic representation of a partial restriction-enzyme map of two recombinant cDNA clones obtained from the IPNV segment A genome in one experiment.

FIG. 3 shows schematically the partial restriction map of cDNA clones obtained from viral genomic segment A in one experiment. The two recombinant plasmids pSp413 and pSp551 contain overlapping sequences from viral segment A RNA. After restriction enzyme digestion, the resulting plasmid DNA fragments are electrophoresed in 1.0-percent agarose or 4-percent NuSieve (FMC Corp.) agarose gels. The gels are stained with ethidium bromide and the sizes of the individual DNA fragments estimated from HindIII-cut λ DNA markers. In FIG. 3, the restriction enzyme cleavage sites are denoted as: A=AvaI, Ac=AccI, E=EcoRI, K=KpnI, N=NcoI, S=SmaI, Nd=NdeI, and X=XhoI.

K. Cross Hybridization Analysis of Recombinant Plasmids

Recombinant plasmids are cleaved with PstI and electrophoresed in horizontal 1-percent agarose gels in Tris-acetate EDTA (TAE) buffer (Maniatis et al., supra. 1982) to separate the cDNA sequences from pUC8 vector DNA. The DNA bands are transferred to nitrocellulose filter paper by the method of Southern (*J. Mol.*

Biol. 98:503–517, 1975) and the filter baked at 80° C. for two hours under vacuum. A labeled nick-translated probe is prepared from a particular transformant and hybridized to the filter as described by Southern. One to two μg of plasmid DNA is added to a 50 μL reaction volume containing 50 mM Tris-HCl, pH 7.5; 20 mM MgCl$_2$; 2 mM μ-mercaptoethanol; 40 μM each dATP, cDTP, dGTP; 2 μM [$^{32}$P]-TTP (300 Ci/mmole); 10 units of E. coli DNA Polymerase I; and DNase titrated for an optimal reaction time of 15 minutes at 15° C. The labeled probe is passed through a Sephadex G-50 column prior to hybridization.

L. Subcloning of cDNA Segment A Into pT7 Vectors

Figure 4:
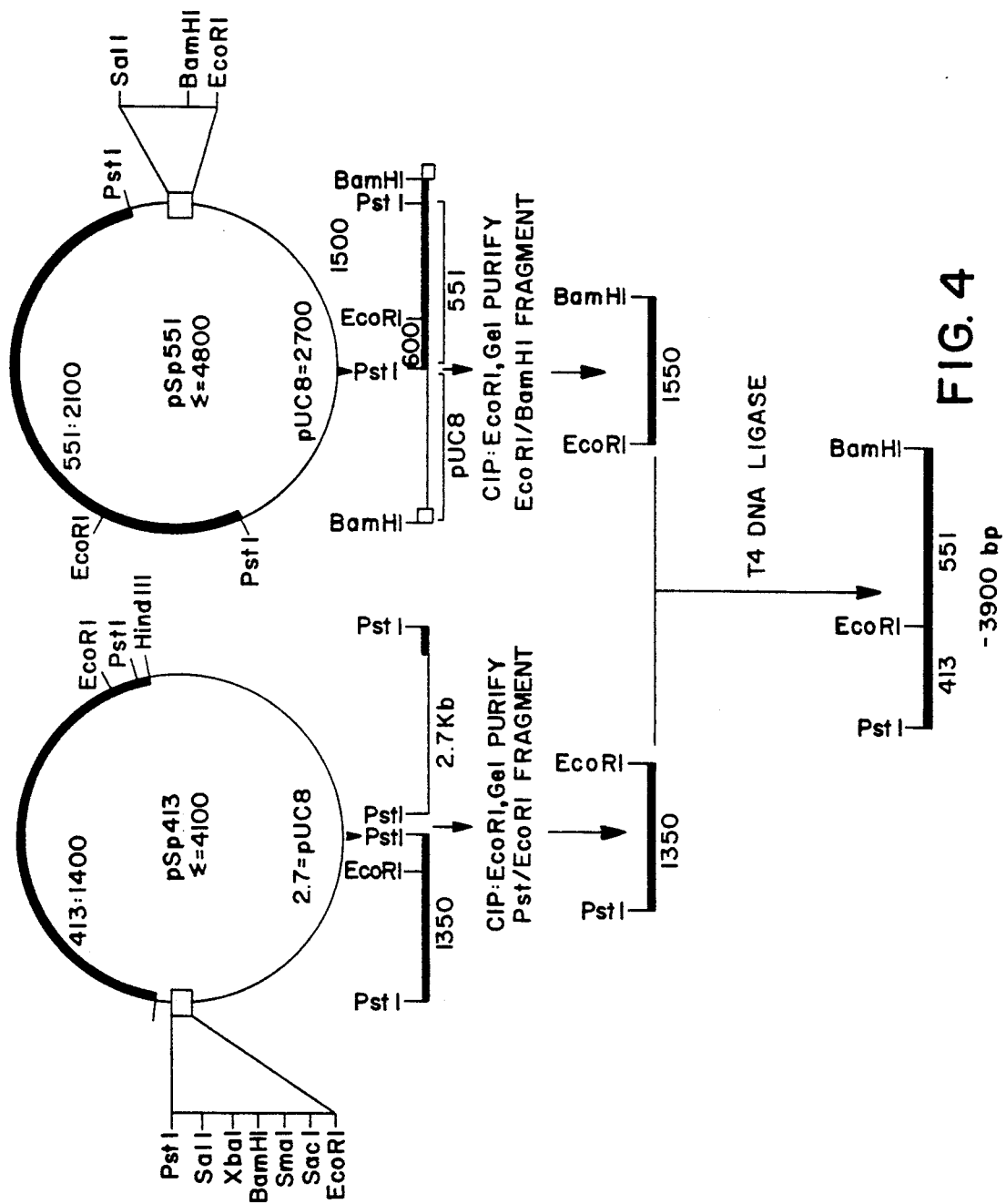
FIG. 4 schematically depicts the separation of the two overlapping inserts from pSp413 and pSp551 from pUC8 sequences by digestion with PstI and BamHI and ligated together at their common EcoRI site with T7 DNA ligase.
Figure 5:
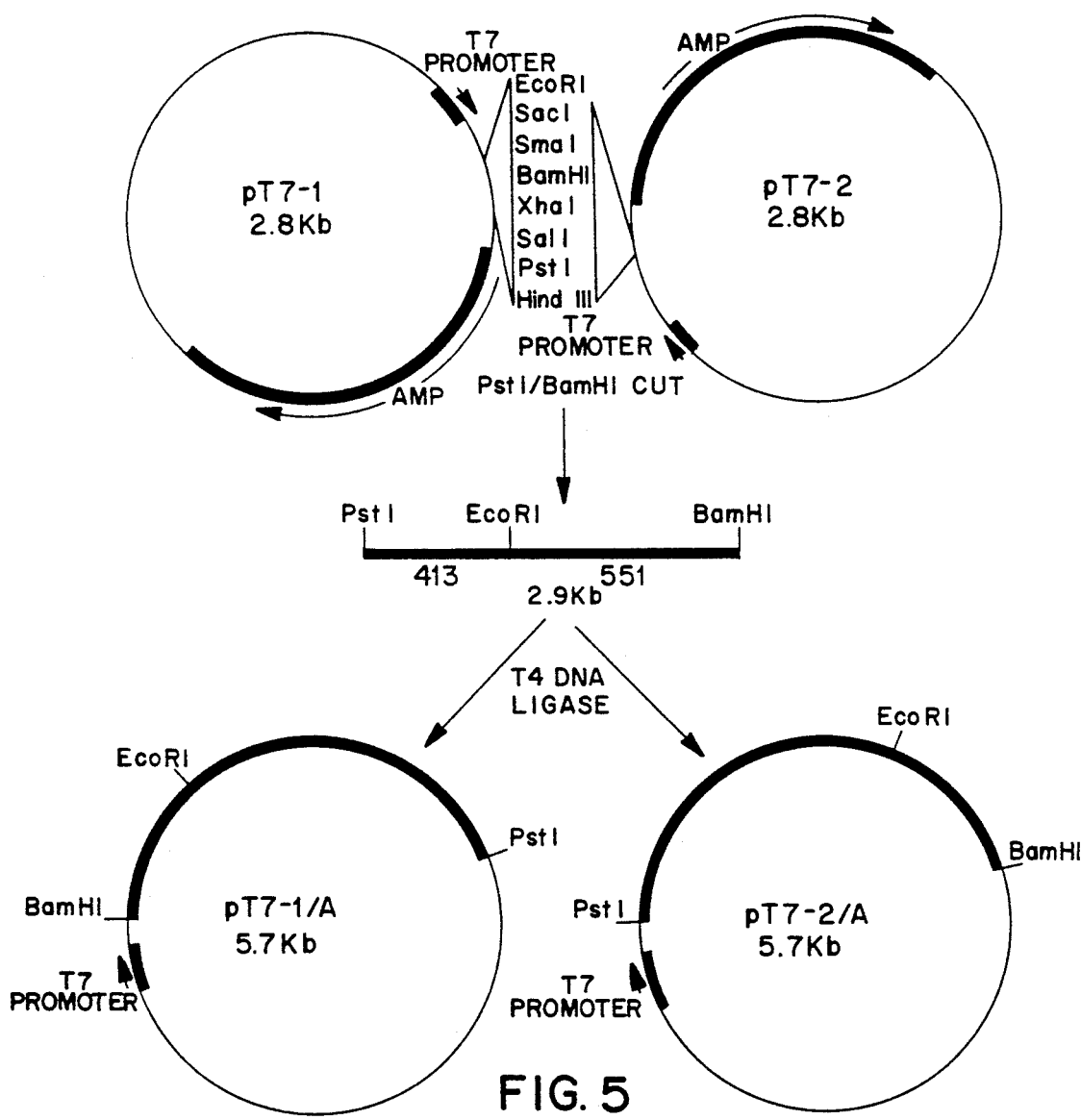
FIG. 5 schematically depicts the subcloning of the complete segment A cDNA produced as shown in FIG. 4 into the T7 RNA polymerase vectors pT71 and pT72.
Figure 6:
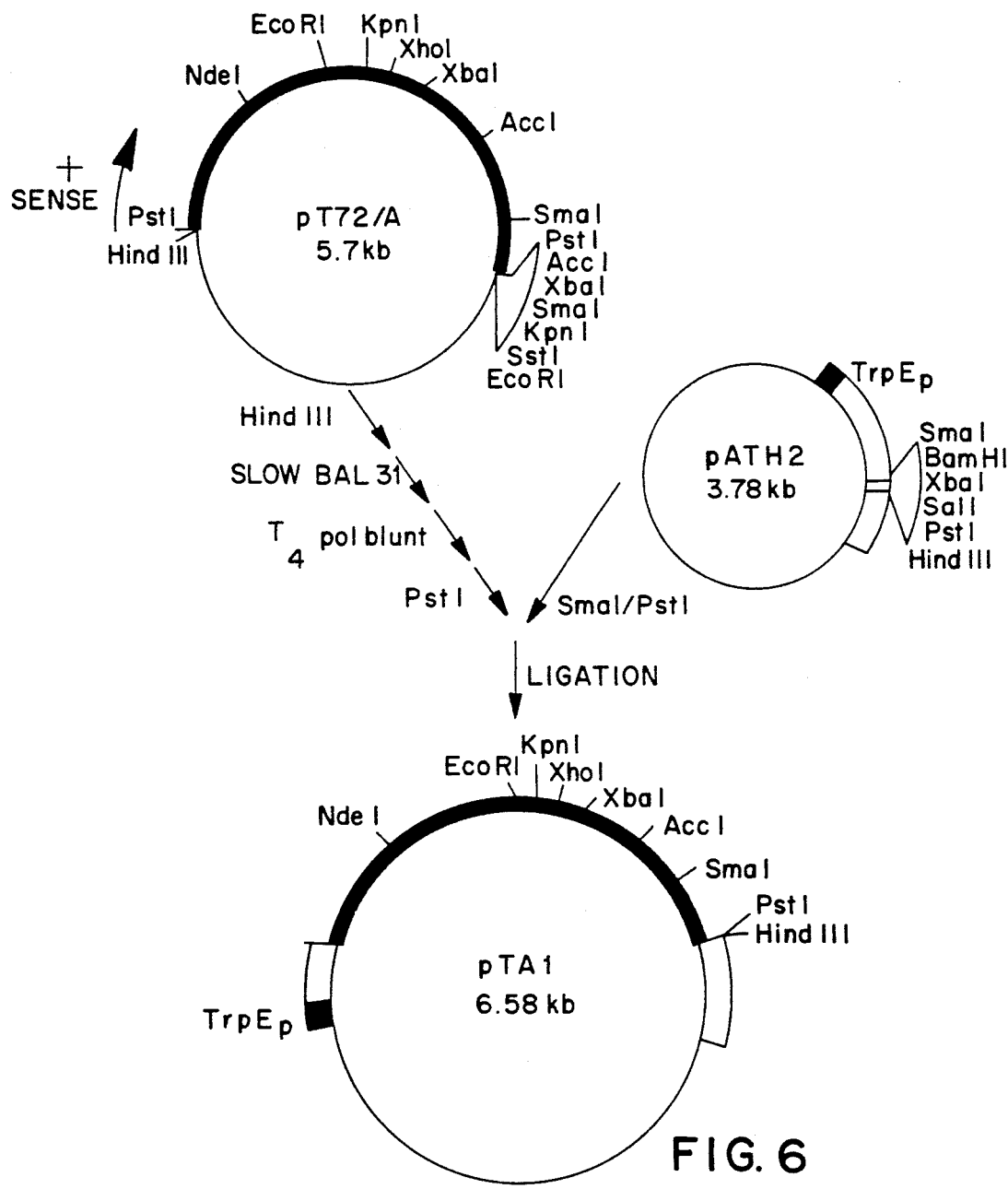
FIG. 6 is a schematic representation of the cloning of segment A cDNA from pT72-A into the TrpE-fusion expression vector pATH2.

As shown schematically in FIG. 4, the two overlapping inserts from plasmids pSp413 and pSp551 that cross-hybridized to IPNV segment A RNA were ligated together at the common EcoRI site and then subcloned into the T7 RNA polymerase vectors, pT71 and pT72 (FIG. 5). These vectors contain the promoter for T7 bacteriophage RNA polymerase which can be used to synthesize RNA transcripts in vitro.

To perform this procedure, plasmids pSp413 and pSp551 are cleaved with PstI and BamHI, respectively. The free ends are phosphatased using calf intestinal phosphatase, extracted once with phenol/chloroform-:isoamyl alcohol, and precipitated in ethnol. Both DNAs are then cleaved with EcoRI. After electrophoresis on a 1-percent agarose gel, individual DNA fragments are sliced out and electrophoresed into an ISCO chamber in Tris-borate buffer (Maniatis, supra, 1982) using 7 mA current for 20–60 minutes. The DNAs are extracted with phenol/chloroform:isoamyl alcohol as described above and precipitated in ethanol. The two fragments are mixed at a 1:1 molar ratio and ligated with T4 DNA ligase. Plasmid vectors pT71 and pT72 (cut with BamHI and PstI) are each added to one-half the ligated segment A DNA in the presence of phenol/-chloroform:isoamyl alcohol and the extraction continued. After precipitation in ethanol, the mixed DNAs are ligated and used to transform freshly prepared competent SC181 cells. The transformed cells are plated onto LB agar plates supplemented with 120 μg/mL ampicillin. Ampicillin-resistant colonies are screened by the toothpick/alkaline lysis method (Kurath et al., J. Virol. 53:469–476, 1985) for DNA inserts. The orientation of the recombinant plasmids is determined by restriction enzyme analysis.

The resulting subclones from one experiment were designated pT71/A and pT72/A. These subclones contained the A Segment cDNA insert in opposite orientations relative to the T7 promoter. Each pT7 subclone contained a cDNA insert bordered by poly-DG/dC tails and PstI sites. The T7 RNA polymerase promoter was located just outside the polylinker region of the pT7 plasmids and added a number of nucleotides to the 5' end of single-stranded RNA produced from the plasmids by T7 RNA polymerase For pT71/A, this represents 50 bases; for pT72/A, 53 bases. In vitro translation of the RNA from both subclones showed that pT71/A and pT72/A represent the (−) and (+) strands, respectively, of IPNV Segment A RNA.

M. Construction of Segment A-Containing Expression Vector pTAl

The Segment A cDNA from pT72/A is cloned into the TroE-fusion expression vector pATH2 as shown in FIG. 6. The plasmid pT72/A is first cut with HindIII. The 5′ end is digested with slow Bal31 under conditions specified by the manufacturer (IBI) to remove noncoding regions and to randomly generate fusions in each reading frame, thereby yielding deletions of between zero and 200 bp. Then, following phenol extraction and ethanol precipitation, the Bal31-digested plasmid DNA is treated with T4 DNA polymerase to assure blunt ends. After another phenol extraction and ethanol precipitation, the DNA is digested with PstI and combined with PstI/SmaI-digested pATH2. After hybridization and ligation, the resulting plasmids are transformed into competent *E. coli* HB101 cells and screened immunologically for expression of viral proteins by the colony blot immunological screening assay described below. In one experiment, a single colony giving a very strong positive signal was obtained and designated pTAI ("TA" for TrpE-A Segment fusion).

HB101 cells containing the pTAl plasmid have been placed on deposit with the American Type Culture Collection, Rockville, Md. 20852, USA, the deposit having ATCC Accession Number 67875.

N. Colony Blot Immunological Screening Assay

Immunological screening of bacterial colonies is performed by a modification of the method of Helfman et al. (*Proc. Natl. Acad, Sci. USA* 80:31–35, 1983). Colonies are replicated onto 82-mm nitrocellulose membranes. The replicas are grown overnight at 37° C. on LB agar supplemented with 120 μg ampicillin/mL and 1 mM isopropylthio-β-D-galactoside (IPTG). Bacterial colonies are lysed by exposure to chloroform vapors for 30 minutes, followed by incubation for one hour in blocking/lysis solution (50 mM Tris-HCl, pH 7.5, 150 mM NaCl, 5 mM $MgCl_2$, 3-percent gelatin, and 1 μg DNase and lysozyme 40 μg per mL). The membranes are then rinsed twice in TBS (20 mM Tris-HCl, pH 7.5, 500 mM NaCl) followed by incubation for one hour in a 1:1000 dilution of anti-IPNV sera in TBS. Membranes are rinsed again in TBS and then incubated for 30 minutes in 1:1000 dilution of goat anti-rabbit IgG-horse radish peroxidase conjugate. After two final rinses in TBS, the membranes are developed by incubation in 4CN (10 mL of 3 mg/mL 4-chloro-1-naphthol in methanol, 50 mL TBS, 60 μL hydrogen peroxide). Developed membranes are rinsed in water and air dried.

O. Construction of pUC19 Recombinants Containing Segment A in Positive Sense Orientation The entire A Segment cDNA insert is also cloned into the plasmid vector pUC19 (Yanisch-Perron et al., *Gene* 33: 103–119, 1985) as shown in FIG. 7. The IPNV cDNA is excised from pT72/A by digestion with PstI, followed by isolation by electrophoresis on a 1-percent agarose gel. The cDNA is ligated in-gel (Struhl, *BioTechniques* 3:452–453, 1985) with PstI-digested pUC19 previously treated with calf intestinal phosphatase. The ligation reaction is transformed into competent *E. coli* JM107 cells (Yanisch-Perron, supra). Transformants are plated on LB-amp plates (LB agar plates with 120 μg/mL ampicillin) and, after overnight incubation at 37° C., the resulting colonies are replica-plated onto nitrocellulose membranes These membranes are overlayed onto LB-amp plates containing 0.5 mM isopropylthio-β-D-galactoside (IPTG) as an inducer of the LacZ promoter Induced transformants are screened for expression of viral proteins by the colony blot immunological screening assay.

Figure 7:
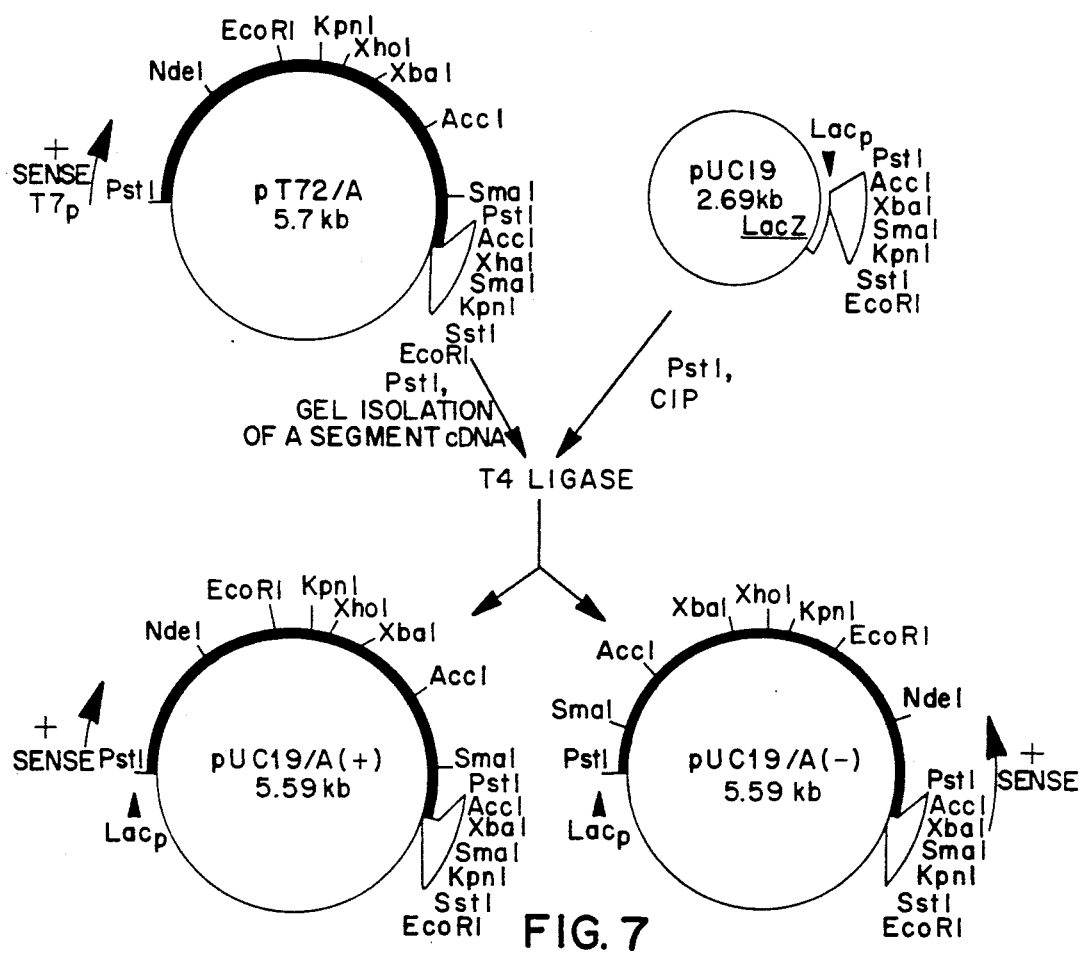
FIG. 7 is a schematic representation of the cloning of the A segment cDNA from pT72/A into the plasmid vector pUC19, showing the generation of plasmids pUC19/A(+) and pUC19/A(−) having the inserted A segment in the positive and negative sense orientations, respectively.

In one experiment, only four transformants gave strong positive signals by the immunoassay and were selected for further analysis. Plasmid preparations were made for each transformant clone and initial restriction analysis was conducted by separate digestions with PstI and AccI. These digests indicated that all of the clones analyzed contained the cDNA insert oriented so that the nonsense strand was under LacZ promoter control. One of these clones was designated pUC19/A(−)(FIG. 7) and additional restriction enzyme analyses with KonI, NdeI, XhoI and EcoRI confirmed the orientation of this construction. Since none of the clones analyzed contained the A Segment cDNA in the positive sense orientation to the LacZ promoter, it was suspected that induction of viral gene expression might be toxic to the cells. Thus, the construction of pUC19 recombinants containing the A Segment cDNA insert was repeated under conditions in which induction of the LacZ promoter was restricted. Transformants replicated onto nitrocellulose membranes for immunoassay were grown on noninducing media (lacking IPTG) until colonies were approximately 1 mm in diameter. The membranes were then transferred to inducing media containing IPTG for 4 hours before being assayed by the colony blot immunological screening assay. Six darkly staining colonies were selected for further analysis. Of these, four were found to be in the positive sense orientation to the LacZ promoter. One of these clones was designated pUC19/A(+)(FIG. 7) and additional restriction enzyme analyses confirmed this construction.

P. Construction of Plasmids Containing 3' Deletions in Segment A DNA

In each of the described pUC19 plasmids, restriction sites which occur once in the Segment A cDNA and once in the flanking multiple cloning site permit the construction of ordered deletions in the cDNA.

Figure 8:
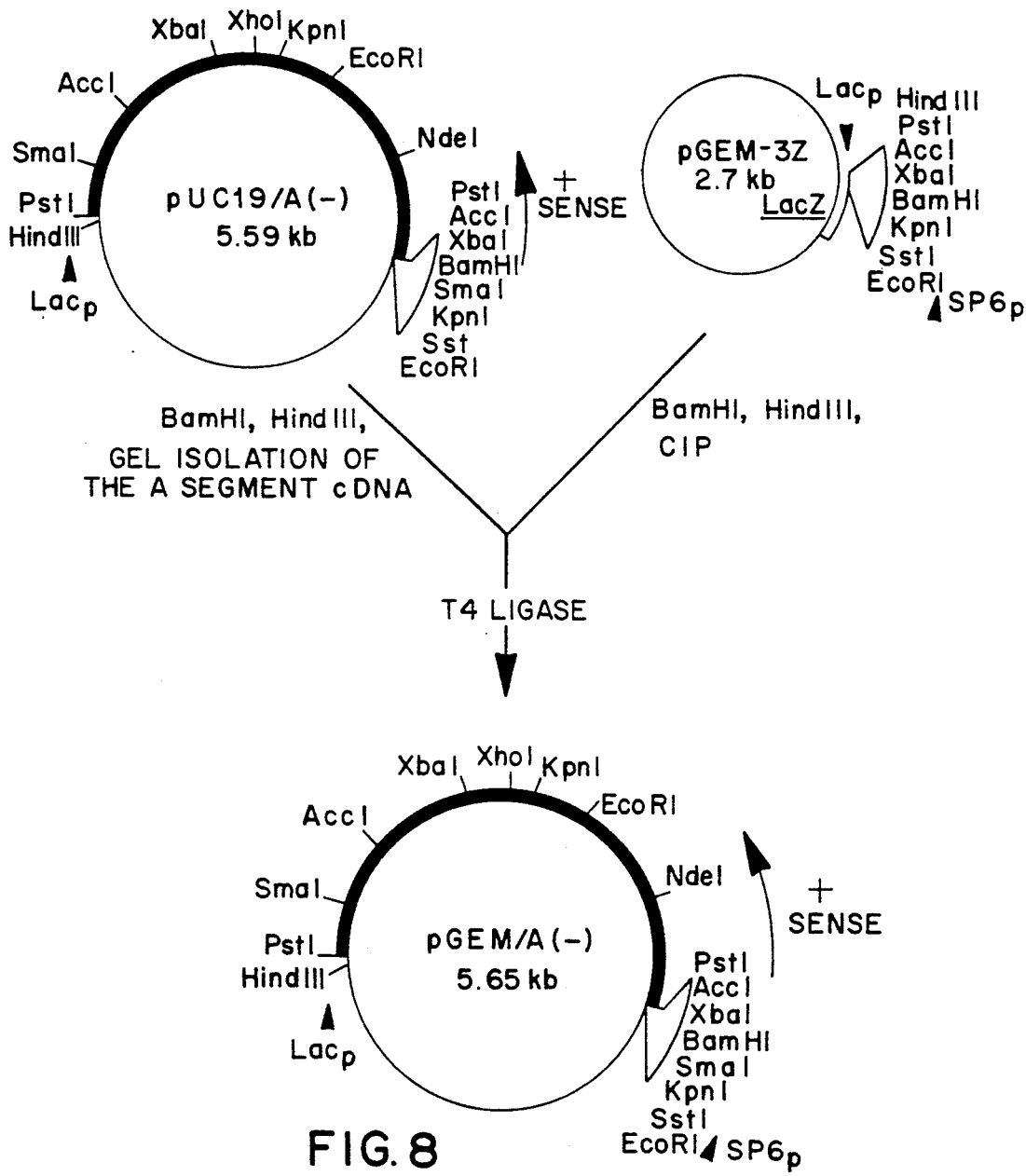
FIG. 8 is a schematic representation of the insertion of the universal translational terminator 5'TAAT-TAATTAAGCT into pUC19/A(+) to produce the recombinant plasmid pUC19/A(+)S.

Prior to construction of a 3' deletion series, an oligodeoxynucleotide containing translational stop codons in all three reading frames is inserted into the SstI site of pUC19/A(+) near the 3' end of the Segment A insert (FIG. 8). This is done to prevent the fusion of the cDNA open reading frame with downstream vector sequences. For example, the oligomer containing the sequence 5'TAATTAATTAAGCT may be used; self-annealing of this oligomer yields double-stranded fragments with 5'AGCT as a 3' overhang at each end. The oligomer is kinased and ligated onto SstI-digested pUC19/A(+) DNA that had been previously treated with alkaline phosphatase. Transformants are screened by restriction endonuclease analysis for the presence of the oligomer by the loss of the SstI site and the creation of a new HindIII site. The creation of the HINdIII site indicates the insertion of more than one oligomer since ligation of two or more of the oligomers·together will result in the formation of this site. In one experiment, eight transformants had lost the SstI site, but only one had the addition of a HindIII site. The clone containing the additional HindIII site was designated pUC19/A+S ("S" for stop codon).

To construct 3′ deletions, pUC19/A+S is digested separately with SmaI, AccI, XbaI, XhoI/SalI, KpnI and EcoRI. The digested plasmids are separated from the fragments on agarose gels, ligated in-gel and transformed into competent JM107 cells. Transformants are analyzed by restriction enzyme digestion to confirm the construction of the desired deletion.

The Segment A cDNA coding regions remaining in each of the plasmids resulting from one experiment are shown in FIG. 9. The deletants were designated pUC19/A+SΔS, pUC19/A+SΔA, pUC19/A+SΔXb, pUC19/A+SΔXo, pUC19/A+SΔK, and pUC19A(+)ΔE. The cDNA region remaining in each of the plasmids was followed by a termination codon provided by the oligonucleotide. The plasmid pUC19/A(+)ΔE did not contain the translational terminator sequence and, as a result, the A Segment open reading frame (ORF) was fused with 54 codons of out-of-phase LacZ sequence.

Q. Western Blot Analysis of Virus-Specific Polypeptides Expressed by Cultures Containing pUC19/A(+) and its Derivatives The polypeptides from induced cultures of JM107 cells containing pUC19/A(+), pUC19/A+S and pUC19/A+S deletion plasmids were compared by Western blot analysis with anti-IPNV, anti-β (anti-VP2) and anti-γ (anti-VP3 and anti-NS) sera (FIGS. 10, 11 and 12, respectively). The pUC19/A(+) and pUC19/A+S cultures (Lanes 3 and 4 in each figure) contained immunoreactive polypeptides corresponding to the $\gamma_1$ (VP3) and $\gamma_{1a}$ proteins. These polypeptides reacted with both the anti-IPNV serum and the anti-γ serum. The polypeptide comigrating with $\gamma_1$ appeared to be a bacterially expressed $\gamma_1$ (VP3), but the polypeptide comigrating with $\gamma_{1a}$ may be either $\gamma_{1a}$ or $\gamma_2$ (NS) since these proteins migrate near each other and the antisera reacts with both. Huang et al., *J. Virol.* 60:1002–1022, 1986.

The culture containing the plasmid deleted to the SmaI site, pUC19/A+SΔS, produced a polypeptide that migrated slightly faster than $\gamma_1$ (approximately 30 kD) and was recognized by the anti-γ serum (FIG. 12, Lane 5). Since approximately 470 bp of the $\gamma_1$ (VP3) protein coding region were deleted in this plasmid, this polypeptide must contain primarily $\gamma_2$ (NS) peptide sequences.

The pUC19/A+S culture also contained two polypeptides of approximately 50 and 55 kD that were detected weakly with both the anti-IPNV and the anti-β sera (Lane 3, FIGS. 10 and 11, respectively). The presence of these polypeptides was unaffected by the 3′ deletions (Lanes 5–10, FIGS. 10 and 11). Thus, they appeared to be β (VP2) polypeptides that terminate prior to the EcoRI site. In view of these results, a "VP2 protein" or "VP2 polypeptide" as used herein can be regarded as either the entire VP2 protein as produced from IPNV mRNA or any portion of the entire protein that immunologically reacts with anti-β serum and, therefore, would be expected to confer immunity to IPNV infection if inoculated into a susceptible host.

The pUC19/A+SΔA culture (Lane 6) contained a polypeptide of approximately 83 kD that reacted with all three antisera. This polypeptide was significantly larger than any of the virion proteins encoded by the A Segment. The reaction of both the anti-β and anti-γ sera with this polypeptide strongly suggested that it was a bacterially expressed truncated precursor polyprotein (t-pp). (This peptide is referred to as t-pp(AccI)). The production of a truncated polyprotein by pUC19/A+SΔA but not by pUC19/A+SΔS suggested that deletion of the region between the SmaI and AccI sites had resulted in the loss of the viral protease activity (NS protein) responsible for processing the polyprotein. This result also indicates that immunologic reactivity with various IPNV antisera, including antisera to capsid proteins, can still occur even when IPNV polypeptides or portions thereof are not folded into their normal configurations.

The plasmids pUC19/A+SΔXb, pUC19/A+SΔXo and pUC19/A+SΔK produced polypeptides that, along with t-pp(AccI), formed a series with decreases in molecular weight corresponding to the decreasing region of the cDNA that remained in each plasmid. The plasmid pUC19/A+SΔXb produced a polypeptide of approximately 72 kD which was recognized by all three antisera. The plasmid pUC19/A+SΔXo produced a polypeptide of approximately 66.5 kD which was detected weakly with the anti-IPNV and anti-β sera but not with the anti-γ serum. The plasmid pUC19/A+SΔK produced a polypeptide of approximately 62 kD which also reacted with only the anti-IPNV and anti-β sera. Since pUC19/A+SΔXo produced a polypeptide slightly larger (66.5 kD) than $\beta_1$ (63 kD) and pUC19/A+SΔK produced a polypeptide slightly smaller (62 kD) than $\beta_1$, it was concluded that the end of the β coding region must lie between the KpnI and XhoI restriction sites.

Figure 9:
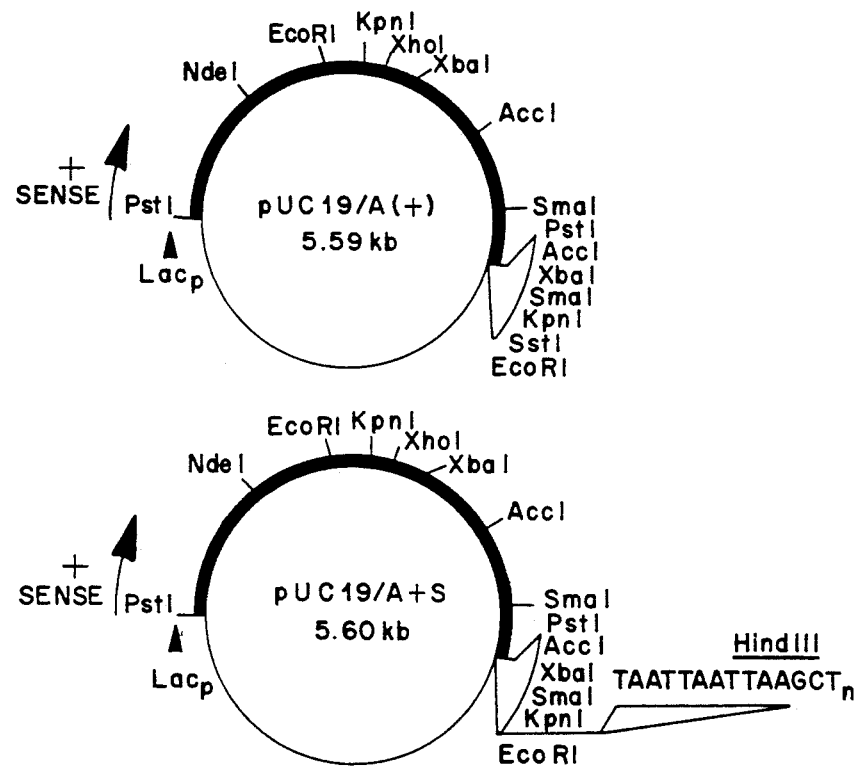
FIG. 9 is a schematic representation of a series of pUC19/A(+)S deletion mutants constructed by deletions of nucleotide sequences from the 3' end of the A segment.
Figure 9:
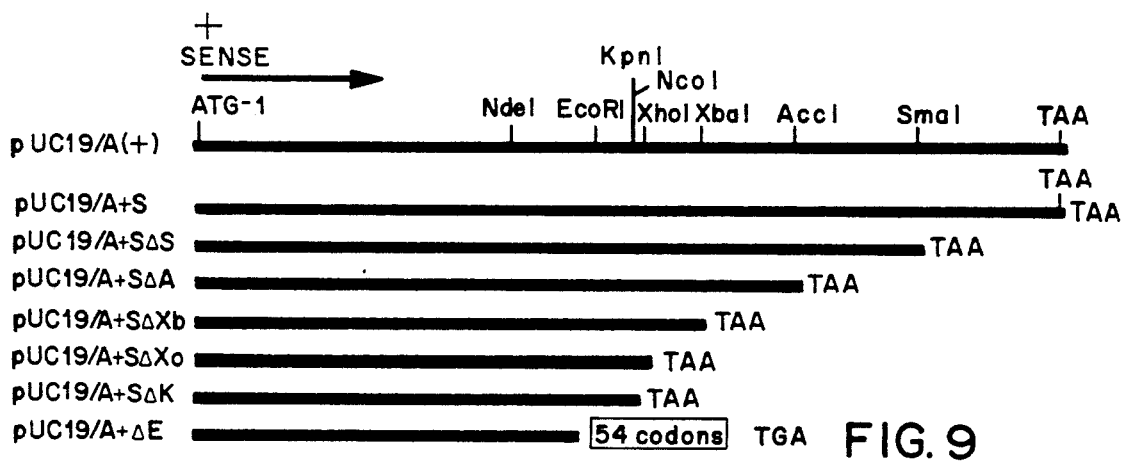
Figure 10:
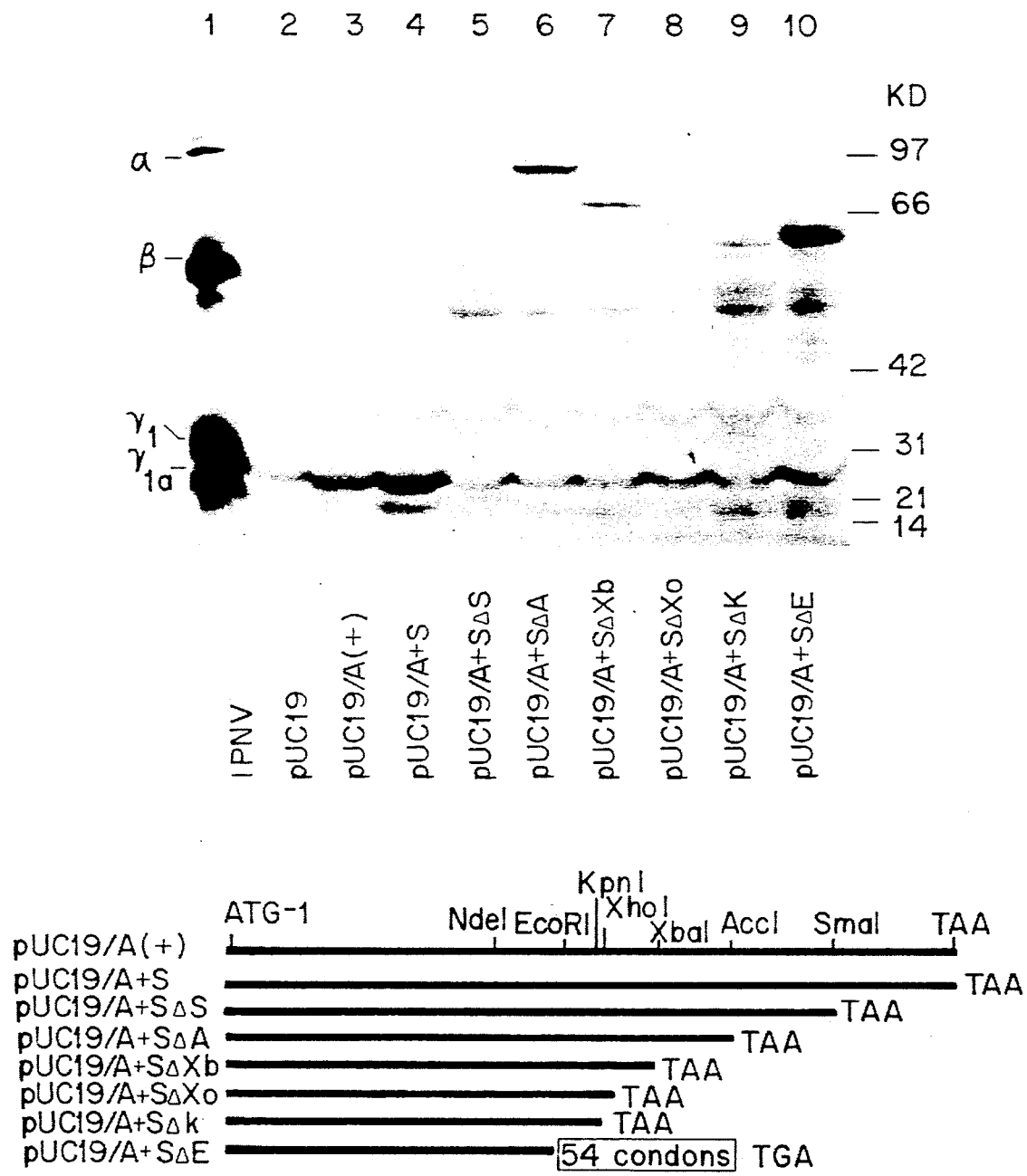
FIG. 10 shows a Western blot analysis of polypeptides produced from induced cultures of JM107 cells containing various 3' deletion mutants from FIG. 9 using anti-IPNV serum.
Figure 11:
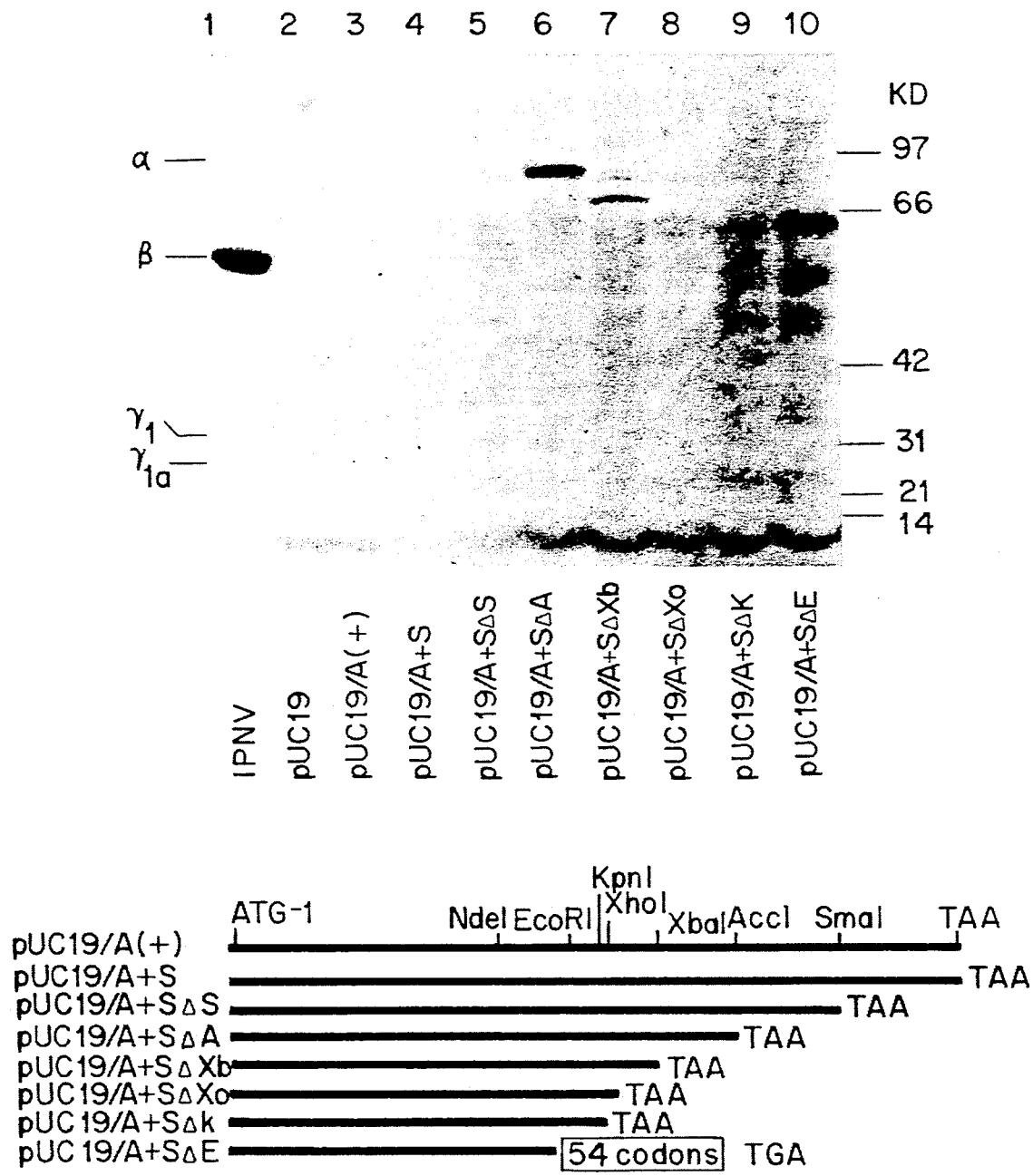
FIG. 11 shows a Western blot analysis of polypeptides produced from induced cultures of JM107 cells transformed with various 3' deletion mutants of FIG. 9 using anti-β serum.
Figure 12:
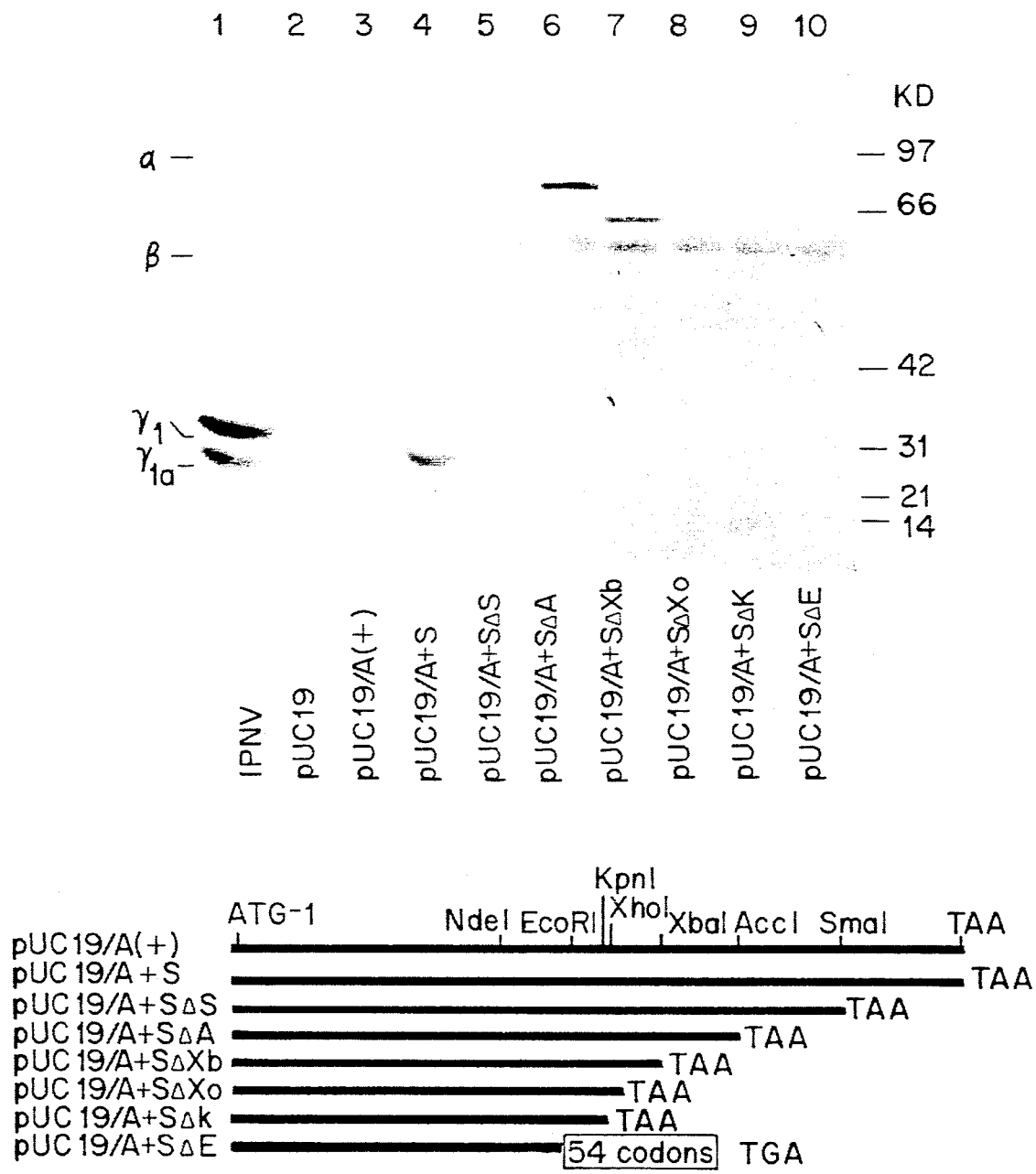
FIG. 12 shows a Western blot analysis of polypeptides produced from induced cultures of JM107 cells transformed with various 3' deletion mutants of FIG. 9 using anti-γ serum.

The pUC19/A+SΔE culture contained a polypeptide of approximately 65 kD that produced a strong signal with the anti-IPNV and anti-β sera but was not recognized by the anti-γ serum. This polypeptide was larger than the one produced by pUC19/A+SΔK, although pUC19/A+SΔE contained less of the cDNA coding region. The larger size of this polypeptide can be accounted for by the 54 additional codons provided by out-of-phase LacZ gene sequences (FIG. 9).

The results obtained with deletants indicate that portions of IPNV capsid proteins retain immunologic reactivity with various anti-IPNV antisera, including anti-capsid protein antisera. Hence, it is expected that IPNV capsid proteins lacking sequences found in complete IPNV capsid proteins will be able to confer immunity to IPNV infection in susceptible hosts.

R. Production of Antigens for Vaccine Trial

Overnight cultures of JM107/pUC19, JM107/pUC19A+S, JM107/pUC19A+SΔA and HB101/pTA1 were grown in LB-amp at 37° C. A 1 mL sample of each of the overnight cultures was inoculated into 1 L of growth medium. For the pUC19, pUC19/A+S, and pUC19A+SΔA cultures, the growth medium was LB-amp with twice the normal concentration of tryptone. The pTA1 culture was grown in supplemented M9 medium. All cultures were grown to an $OD_{600nm}$ of 0.6 before induction. The pUC19 plasmids were induced by the addition of IPTG to a final concentration of 2.5 mM. The pTA1 culture was induced by the addition of isoamyl alcohol to a final concentration of 2 μL. Incubation of the cultures was continued overnight at 37° C. The cultures were centrifuged for 5 minutes at 5000 rpm in a Sorvall GSA rotor. The supernatant fluid was decanted and the cells were resuspended in 1/100 volume lysis buffer (10 mM $MgCl_2$, 5 μg/mL DNAse, 20 μg/mL lysozyme and 100 mM $NaPO_4$ buffer, pH 7.5) and incubated on ice for 1 hour. The cell suspensions were then sonicated three times for 20 seconds each at 40 watts (Heat Systems Ultrasonic, microtip). The bacterial lysates were assayed for the presence of viral antigens by Western blot analysis (FIG. 13).

To perform the Western blot analysis, samples of 1, 5 and 25 μL of each of the sonicated cell lysates, each lysate having a substantially identical concentration of total cell protein, are separated by sodium dodecyl sulfate polyacrylamide gel electrophoresis (SDS-PAGE), electro-phoretically transferred to nitrocellulose (Towbin et al., *Proc. Natl. Acad Sci. USA* 76:4350–4354, 1979) and then analyzed with anti-IPNV serum. The nitrocellulose membrane is treated with 3-percent gelatin in TBS (20 mM Tris-HCl, pH 7.5, 500 mM NaCl) for 20 minutes and then rinsed three times in TBS. Separate membrane strips containing the transferred viral proteins are incubated for 1.5 hours in the antisera (anti-α, anti-β and anti-γ) which had been diluted 200-fold. A membrane strip is also incubated in antiserum raised against whole virions, anti-IPNV (Huang et al., *J. Virol.* 60:1002–1011, 1986), which had been diluted a thousand-fold. The strips are rinsed three times in TBS. The strips are then incubated for 30 minutes in a 1:1000 dilution of goat anti-rabbit IgG conjugated to horseradish peroxidase (GAR-HP), washed three times and developed in substrate solution 4CN (10 mL of 3 mg/mL 4-chloro-1-napthol in methanol, 50 mL TBS, 60 μL $H_2O_2$). The developed membranes are rinsed in water and dried.

Figure 13:
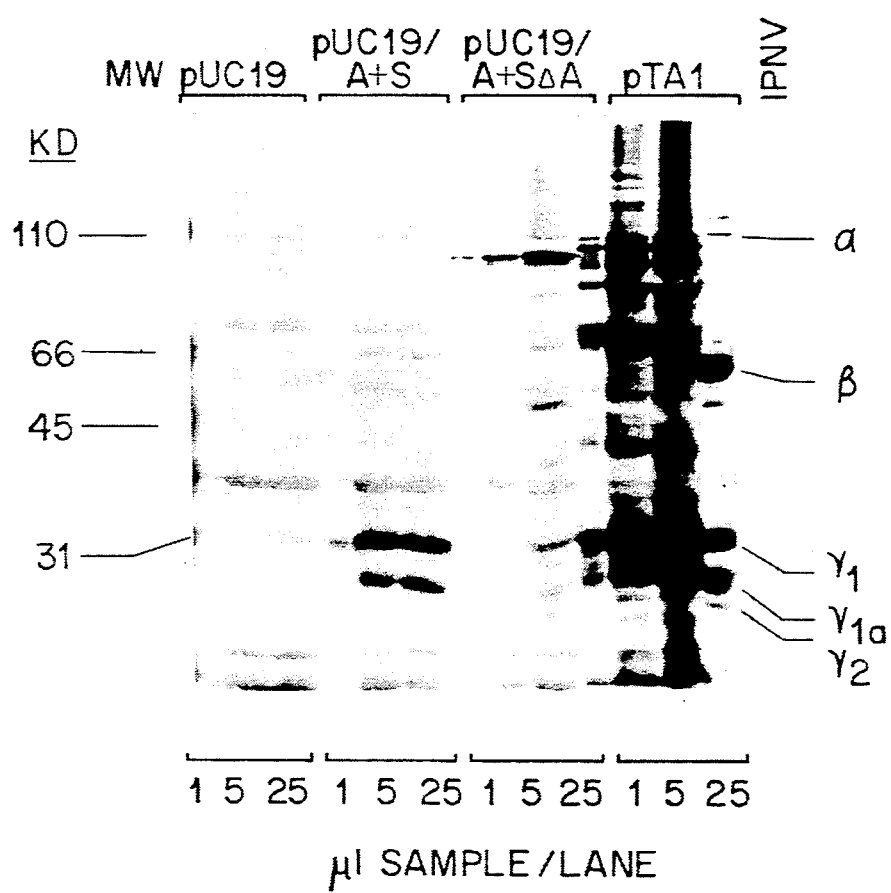
FIG. 13 shows a Western blot analysis of bacterially expressed viral antigens used in a vaccination trial.
Figure 14:
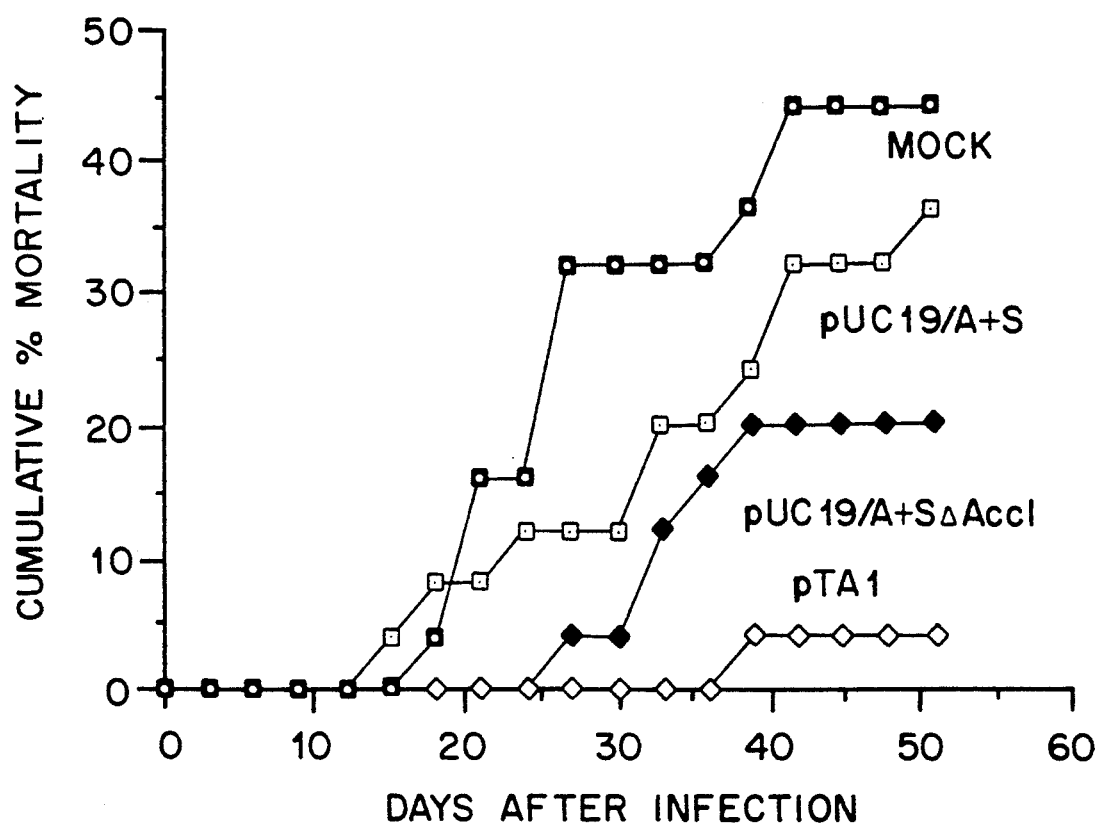
FIG. 14 is a plot of the cumulative percent mortality experienced by rainbow trout at various days post-infection with IPNV after previous vaccination with lysates from pUC19 cells transformed with various segment A-containing plasmids.

In FIG. 13, the pUC19 lanes show the background produced by bacterial proteins. In the pUC19/A+S lanes, the antiserum reacted with two bands comigrating with $\gamma_1$ (VP3) and $\gamma_{1a}$. There was also a weak signal from a band corresponding to $\beta_1$ (VP2), indicating a low rate of production of VP2, possibly due to inefficient translational initiation. In the pUC19/A+SΔA lane, the antiserum reacted with the 83 kD t-pp(AccI) protein. Note the absence of bands corresponding to $\gamma_1$ or $\gamma_{1a}$. This is because the pUC19/A+SΔA deletant, being a 3' deletion mutant, lacks the $\gamma_1$ (VP3) and a portion of the $\gamma_2$ (NS) coding sequences. Consequently, this deletant produces essentially only VP2 in the form of a truncated precursor polypeptide larger than actual VP2, presumably containing both VP2 and a portion of the NS protein. The quantity of viral antigen present in pTA1 lanes was substantially greater than that of either the pUC19/A+S and pUC19/A+SΔA lanes. The quantity of viral antigens present in the 5 and 25 μL lanes was so great that it was difficult to distinguish individual bands. In the lane containing the 1 μL sample of pTAI lysate proteins, individual bands can be seen which correspond in molecular weights to $\beta_1$ (VP2, 63.5 kD), $\gamma_1$ (VP3, 32 kD) and $\gamma_{1a}$ (28.5 kD). Polypeptides of 75, 81, 87 and 93 kD were also detected by the antiserum.

To produce rabbit antisera to IPNV proteins, purified IPNV (1.5 mg) is suspended in 2 mL of 6 M guanidine hydrochlorid-0.1-percent β-mercaptoethanol. The solution is incubated at 25° C. for 20 hours and then 37° C. for one hour. Dissociated proteins are separated on a Sephadex G-200 column with 6 M guanidine hydrochloride-0 1-percent β-mercaptoethanol as the elution buffer. Samples from the column fractions are analyzed on silver stained SDS-PAGE gels. Allen, *Electrophoresis* 1:32–37, 1980. Fractions containing viral proteins from the β, γ and α size classes are pooled separately and fractions containing proteins from more than one size class are discarded. The pooled fractions are concentrated to a final volume of 0.5 mL, and emulsified with an equal volume of Freund's complete adjuvant. Each emulsion is injected subcutaneously at three sites along the back of a New Zealand White rabbit. The fractionation procedure is repeated with 0.6 mg of viral protein. The resulting fraction pools are emulsified in Freund's incomplete adjuvant and injected four weeks after the initial immunization. Serum samples are collected two weeks after the second immunization. The resulting sera are designated anti-α, anti-β and anti-γ and can be tested for reactivity with the viral antigens by Western blot analysis

S. Vaccine Trial with Bacterially Expressed Viral Antigens

Lysates of induced cultures of pTAI, pUC19/A+S and pUC19/A+SΔA were used in a study of the efficacy of bacterially expressed viral polypeptides as a vaccine for IPNV. A lysate of an induced culture of pUC19 was used as a mock-infection control. The concentration of total cell protein in each lysate inoculum was substantially identical to permit comparisons of immunogenic efficiency.

Rainbow trout (*Salmo gairdneri*) fry were used for vaccine trials. The average weight of the fry was 0.13 g at the beginning of the experiment. The fry were divided into groups of 25 fish and each group was held in an 18 L aquarium throughout the course of the experiment. The fish were fed Oregon Biodiet No. 2 at 2- to 4-percent body weight per day. Water temperature was 10°-11° C.

Each of the bacterial lysates was used for vaccination of 25 rainbow trout fry by immersion. Vaccination was by immersion. The water level in the tanks was lowered to approximately 800 mL and 25 mL of the bacterial lysate (described above) was added. Exposure to the vaccine was for 20 minutes at this concentration; the water level was increased to approximately 6 L for 15 minutes and then to 18 L for 20 minutes before water flow was resumed.

Twenty days after the vaccination, the fry were challenged with the Buhl strain of IPNV. Virus were added to tanks at a concentration $10^{-5}$ plaque forming unit per mL in 3 L of water and maintained at this level for 18 hours. The water level was then raised to 18 L and the challenge was continued in static water (except that flow would be resumed for several hours once a week to clean tanks).

Moribund fish were collected on a daily basis for 54 days. The presence of virus in all of these fish was confirmed by the production of characteristic cytopathic effect in tissue culture. FIG. 14 shows a plot of the cumulative mortality in each group versus the number of days after the challenge. In the mock (pUC19) treated group, the total cumulative mortality reached 44 percent by the end of the challenge period. The final cumulative mortality of the pTA1 treated group was only 4 percent. The groups treated with pUC19/A+S and pUC19/A+SΔA had final cumulative mortalities of 36 and 20 percent, respectively. These tests indicate that vaccination of susceptible fish with bacteria-expressed IPNV viral proteins, particularly those of pTA1, provided substantial protection from viral challenge.

The efficacy of each vaccine tested seemed to correlate with the efficiency of VP2 production by each plasmid. For example, where the efficiency of VP2 production by pUC19/A+S was lower than either pTAI or pUC19/A+SΔA, the pUC19/A+S lysate conferred the lowest immunity to the fish. However, since pUC19-infected fish essentially had no enhanced immunity to IPNV infection, it can be concluded that even a relatively low dose of VP2 in a bacterial lysate confers significant immunity in susceptible fish. Also, the effectiveness of any of these vaccines can be improved, if desired, by increasing the concentration of cell lysate in the inoculum.

These experiments also indicated that the minor capsid protein VP3 also contributes some immunogenic effect. It is possible that VP3 actually cooperates with VP2 in enhancing the immunogenic effect of VP2 alone. For example, the pTA1 lysate was an extremely effective vaccine. pTA1 also produced high titers of both VP2 (β) and VP3 ($\gamma_1$). Because VP2 and VP3 are exposed on the icosahedral surface of IPNV and probably interact thereon in a conformational manner that dictates in part the serological characteristics of the virus, it is probable, based on the studies described herein, that a mixture of VP2 and VP3 polypeptides in a bacterial lysate vaccine interact in a manner that presents a more effective neutralizing site than VP2 alone. (A neutralizing site is an antigenic site on a macromolecule or macromolecular aggregate that stimulates the production of neutralizing antibodies in a vaccinated host.) Accordingly, VP2 is immunogenic when in the form of a bacterial lysate. Further tests would likely show that VP3 alone in a bacterial lysate would also confer measurable immunity to susceptible fish.

T. Nucleotide Sequence of the VP2 Gene

To determine the nucleotide sequence of the IPNV (Sp strain) VP2 gene, PT72/A was selectively cut with a number of restriction endonucleases and subcloned in both directions in M13 sequencing vectors mp18 and mp19. Sequencing was performed by the ddideoxy chain termination method of Sanger et al., *Proc. Nat. Acad. Sci. USA* 74:5463-5467 (1977) as modified by Davis et al., *Basic Methods in Molecular Biology*, Elsevier, NY (1986). The DNA sequence between the PstI and XhoI sites is shown in FIG. 15. The presumed amino acid sequence of VP2, based upon the nucleotide sequence and the ATG start codon at positions 37-39, is also shown.

Having illustrated and described the principles of my invention, it should be apparent to those of ordinary skill in the art that the specific examples described herein may be modified in detail without departing from such principles.

I claim:

1. A method for immunizing fish against the VR-299 and SP serotypes of the infectious pancreatic necrosis virus (IPNV), the method comprising administering to susceptible fish a vaccine comprised of an IPNV polypeptide consisting essentially of a polypeptide from the viral A segment and including at least VP2, the vaccine being administered in an amount sufficient o induce immunity to subsequent infection by IPNV, wherein said polypeptide having been produced in a bacterial host by an expression vector compatible with the host, the expression vector including an inserted DNA sequence from said A segment of the viral DNA coding for the IPNV polypeptide in the vaccine.

2. The method of claim 1 wherein the step of administering comprises adding the vaccine to water containing the fish, the vaccine subsequently passing from the water into the bodies of the fish.

3. The method of claim 2 wherein the step of administering the vaccine is performed on young fish at approximately the time of their first ingestion of food.

4. The method of claim 1 including the steps of:

culturing bacterial cells propagated from competent bacterial cells transformed by an expression vector containing a gene coding for the IPNV polypeptide, the polypeptide capable of inducing immunity in fish receiving the vaccine to subsequent infection by IPNV; and disrupting the cells after an appropriate time to release the IPNV polypeptide produced by the bacterial cells and thereby provide the vaccine.

5. The method of claim 4 wherein the disrupted bacterial cells and contents released therefrom are added to water containing the fish, the resulting concentration of disrupted bacterial cells and contents released therefrom in the water being sufficient to confer immunity to the fish to IPNV infection.

6. The method of claim 5 wherein the disrupted cells and contents released therefrom are used without any purification of IPNV polypeptides from the cell contents.

7. A vaccine for immunizing susceptible fish against infection by VR-299 or SP serotypes of the infectious pancreatic necrosis virus (IPNV), the vaccine comprising an IPNV polypeptide consisting essentially of a polypeptide from the viral A segment and including at least VP2, wherein said vaccine is capable of inducing immunity in the fish to subsequent infection by the VR-299 or SP serotypes of IPNV, said polypeptide being produced by an expression vector in a compatible bacterial host, and the vector including an inserted DNA sequence from the A segment of the viral DNA coding for the IPNV polypeptide in the vaccine.

8. The vaccine of claim 7 including both the VP2 and VP3 polypeptides of IPNV.

9. The vaccine of claim 8 wherein the VP2 protein is at least one size variant of that protein detectable via sodium didecyl sulfate- polyacrylamide gel electrophoresis, the size variants ranging in size from approximately 50 kiloDaltons to 65 kiloDaltons.

* * * * *

UNITED STATES PATENT AND TRADEMARK OFFICE
CERTIFICATE OF CORRECTION

PATENT NO. : 5,165,925
DATED : November 24, 1992
INVENTOR(S) : Jo-ann C. Leong

It is certified that error appears in the above-indentified patent and that said Letters Patent is hereby corrected as shown below:

Column 3, line 40, "operate o relatively" should read --operate on relatively--.

Column 7, line 35, "15 82 M" should read --15 $\mu$M--.

Column 9, line 7, "$\mu$-mercaptoethanol" should read --$\beta$-mercaptoethanol--.

Column 9, line 58, "polymerase" should read --polymerase.--.

Column 10, line 63, "membranes These" should read --membranes. These--.

Column 10, line 66, "LacZ promoter Induced" should read --LacZ promoter. Induced--.

Column 14, line 44, "pTAI lysate" should read --pTA1 lysate--.

Column 14, line 47, "w®re also" should read --were also--.

Column 15, line 36, "$10^{-5}$ plaque" should read --$10^{-6}$ plaque--.

UNITED STATES PATENT AND TRADEMARK OFFICE
CERTIFICATE OF CORRECTION

PATENT NO. : 5,165,925
DATED : November 24, 1992
INVENTOR(S) : Jo-ann C. Leong

It is certified that error appears in the above-indentified patent and that said Letters Patent is hereby corrected as shown below:

Column 16, line 51, "o induce" should read --to induce--.

Signed and Sealed this

Seventh Day of March, 1995

Attest:

BRUCE LEHMAN

Attesting Officer      Commissioner of Patents and Trademarks